US009034887B2

(12) United States Patent
Oliver et al.

(10) Patent No.: US 9,034,887 B2
(45) Date of Patent: May 19, 2015

(54) DIHYDROOROTATE DEHYDROGENASE AS ANTIFUNGAL DRUG TARGET AND QUINAZOLINONE-BASED INHIBITORS THEREOF

(75) Inventors: Jason David Oliver, Wilmslow (GB); John Leslie Thain, Manchester (GB); Michael John Bromley, Halifax (GB); Graham Edward Morris Sibley, Manchester (GB); Michael Birch, Manchester (GB)

(73) Assignee: F2G Limited, Manchester (GB)

( * ) Notice: Subject to any disclaimer, the term of this patent is extended or adjusted under 35 U.S.C. 154(b) by 856 days.

(21) Appl. No.: 12/990,478

(22) PCT Filed: May 1, 2009

(86) PCT No.: PCT/GB2009/001114
§ 371 (c)(1),
(2), (4) Date: Feb. 4, 2011

(87) PCT Pub. No.: WO2009/133379
PCT Pub. Date: Nov. 5, 2009

(65) Prior Publication Data
US 2011/0160231 A1 Jun. 30, 2011

(30) Foreign Application Priority Data
May 1, 2008 (GB) .................................. 0808029.3

(51) Int. Cl.
*A61K 31/517* (2006.01)
*G01N 33/573* (2006.01)
*C12Q 1/32* (2006.01)
*C12N 9/04* (2006.01)
*C07D 239/72* (2006.01)
*A61P 31/10* (2006.01)
*C07D 239/95* (2006.01)
*C12N 9/02* (2006.01)

(52) U.S. Cl.
CPC ............... *C12Q 1/32* (2013.01); *C07D 239/95* (2013.01); *C12N 9/001* (2013.01); *C12Y 103/05002* (2013.01); *G01N 2333/90206* (2013.01); *G01N 2500/02* (2013.01)

(58) Field of Classification Search
None
See application file for complete search history.

(56) References Cited

U.S. PATENT DOCUMENTS 5,976,848 A 11/1999 Davis et al.
6,951,847 B2 * 10/2005 Gibson et al. ................. 514/169

FOREIGN PATENT DOCUMENTS

| WO | WO-02/053728 A2 | 7/2002 |
| WO | WO-02/053728 A3 | 7/2002 |
| WO | WO-02/086090 A2 | 10/2002 |
| WO | WO-02/086090 A3 | 10/2002 |

OTHER PUBLICATIONS

Inglese et al., High-throughput screening assays for the identification of chemical probes. Nature Chemical Biology, 2007, 3, 466-479.*
Miller et al. Dihydroorotate Dehydrogenase (Neurospora). Methods in Enzymology, 1978, 51, 63-69.*
Internet printout of "Bensasson et al., Nanosecond Irradiation Studies of Biological Molecules-I. Coenzyme Q6 (Ubiquinone-30). Photochemistry and Photobiology, 1972, 16, 27-37."*
International Search Report mailed on Oct. 28, 2009, for PCT Patent Application No. PCT/GB2009/001114, filed on May 1, 2009, 8 pages.
Written Opinion mailed on Oct. 28, 2009, for PCT Patent Application No. PCT/GB2009/001114, filed on May 1, 2009, 10 pages.
Bhargava, P.N. et al. (Mar. 1965). "Synthesis of Some S-Substituted 2-Mercapto-3-Aryl-4-Quinazolones," *Bulletin of the Chemical Society of Japan* 38(3):342-344.
Bhargava, P.N. et al. (Mar. 1968). "Some 6,8-Dibromo-S-Substituted-2-Mercapto-3-Aryl(Or Alkyl)-4-Quinazolones," *Journal of Medicinal Chemistry* 11(2):404-405.
Choubey, V.N. (1971). "Studies on 4 (3H) Quinazolones: Synthesis of S-Ethers," *United Arab Republic Journal of Chemistry* 14(4):407-412.
El-Azab, A.S. (2007). "Synthesis of Some New Substituted 2-Mercaptoquinazoline Analogs as Potential Antimicrobial Agents," *Phosphourus, Sulphur, and Silicon* 182(2):333-348.
Gustafson, G. et al. (1996). Database Accession No. PREV199699184967, "Identification of a New Antifungal Target Site Through a Dual Biochemical and Molecular-Genetics Approach," *Current Genetics* 30(2)159-165.
Jira, T. et al. (1996). "Synthesis and HPLC-Separation of Astropisomeric and Central Chiral 3-Aryl-2-Mercapto- and 3-Aryl-2-Alkylthio-4(3H)-Quinazolinone Derivatives on Chiral Stationary Phases. Part I: Synthesis," *Pharmazie* 51(5):273-279. (Translation of Abstract Only).
Lakhan, R. (1969). "Synthesis of Mercaptoquinazoline Derivatives as Potential Antimalarials," *Chemical & Pharmaceutical Bulletin* 17(11):2357-2361.
McCarty, J.E. et al. (Feb. 20, 1960). "Synthesis of Some Thioquinazolones of Interest as Potential Ataractic Agents," *Journal of the American Chemical Society* 82:964-966.
Malmquist, N.A. (Apr. 27, 2007, e-published Feb. 28, 2007). "Detergent-Dependent Kinetics of Truncated *Plasmodium Falciparum* Dihydroorotate Dehydrogenase," *J. Biol. Chem.* 282(17) 21 pages.

(Continued)

*Primary Examiner* — Michael Barker
*Assistant Examiner* — Po-Chih Chen
(74) *Attorney, Agent, or Firm* — Morrison & Foerster LLP

(57) ABSTRACT

A method of identifying an antifungal agent which targets a DHODH protein (alias PyrE, dihydroorotate dehydrogenase, EC: 1.3.99.11) of a fungus comprising contacting a candidate substance with a fungal DHODH protein and determining whether the candidate substance binds or modulates the DHODH protein, wherein binding or modulation indicates that the candidate substance is an antifungal agent. Specific examples concern *Aspergillus fumigatus* and *Candida albicans* DHODH proteins. DHODH inhibitors with a Quinazolinone core are also disclosed.

8 Claims, No Drawings

(56) References Cited

OTHER PUBLICATIONS

Matsuda, H. et al. (Aug. 1992). "Application of Ubiquinone Systems and Electrophoretic Comparison of Enzymes to Identification of Clinical Isolates of *Aspergillus Fumigatus* and Several Other Species of *Aspergillus*," *Journal of Clinical Microbiology* 30(8):1999-2005.

Miller, R.W. et al. (1978). "Dihydroorotate Dehydrogenase (*Neurospora*)," Chapter 9 in *Methods in Enzymology*, Academic Press, Inc., 51: 63-69.

Murav'Eva, K.M. et al. (1965). "Derivatives of 2-Mercapto-4-Quinazolone," *Biol. Aktivin. Soedin., Akad. Nauk. SSSR*, located at <https://stneasy.fiz-karlsruhe.de/tmp/01212943134199/109225462.html>, pp. 54-56. (Caplus abstract CAN 63:88912).

Murav'Eva, K.M. et al. (1967). "Antitubercular 6-Methoxy-2-Mercaptoquinazolin-4-Ones," *Khimiko-Farmatsevticheskii Zhurnal*, located at <http://stneasy.fiz-karlsruhe.de/tmp/01212943134199/24707406.html>, 1(8):29-31. (Caplus abstract CAN 68:114543).

Parker, M.H. et al. (2002). Database Accession No. 136:130162, "The identification and Optimization of Oomycete Dihydroorotate Dehydrogenase Inhibitors as Fungicides," *Synthesis and Chemistry of Agrochemicals VI* 800:303-313. (Abstract Only).

Rao, R.P. et al. (Nov. 1978). "Synthesis of Some $_2$-Alkylthio-$_3$-Aryl-$_4$($_3$H) Quinazolones," *Indian Journal of Chemistry* 16B(11):1023-1025.

Sharma, B.P. et al. (Jul. 2005). "Synthesis of Some New Thioquinazolinone Derivatives of Biological Activity," *Journal of the Indian Chemical Society* 82(7):651-653.

Shukla, S.K. et al. (1984). "Antimicrobial Activity of 2,3-Disubstituted 4 (3H)-Quinazolone Derivatives," *Indian Journal of Forestry* 7(2):151-153.

Suzuki, M. et al. (1998). "Cellular Neutral Sugar Compositions and Ubiquinone Systems of the Genus *Candida*," *Microbiol. Cult. Coll.* 14(2):49-62.

Zameitat, E. et al. (2004, e-published May 25, 2004). "Two Different Dihydroorotate Dehydrogenases from Yeast *Saccharomyces Kluyveri*," *FEBS Letters* 568:129-134.

Zameitat, E. et al. (2006). "Biochemical Characterization of Recombinant Dihydroorotate Dehydrogenase from the Opportunistic Pathogenic Yeast *Candida Albicans*," *FEBS Journal* 273(14):3183-3191.

Zameitat, E. et al. (May 2007). "Functional Expression of Human Dihydroorotate Dehydrogenase (DHDOH) in *pyr4* Mutants of *Ustilago maydis* Allows Target Validation of DHODH Inhibitors In Vivo," *Applied and Environmental Microbiology* 73(10):3371-3379.

\* cited by examiner

DIHYDROOROTATE DEHYDROGENASE AS ANTIFUNGAL DRUG TARGET AND QUINAZOLINONE-BASED INHIBITORS THEREOF

CROSS-REFERENCE TO RELATED APPLICATIONS

This application is the national phase of PCT application PCT/GB2009/001114 having an international filing date of 1 May 2009, which claims priority from United Kingdom application no. 0808029.3 filed 1 May 2008. The contents of these documents are incorporated herein by reference.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
| --- | --- | --- |
| 251502009800Seqlist.txt | Oct. 26, 2010 | 13,933 bytes |

The present invention relates to the antifungal target, dihydroorotate dehydrogenase (DHODH), screening methods for DHODH inhibitors, a specific group of DHODH inhibitors and their use as antifungal compounds, pharmaceutical compositions containing them and their use in medicine, specifically in the treatment of an individual susceptible to or suffering from a fungal infection. In particular the compounds find use in the treatment of systemic or topical fungal infections, e.g. caused by fungi of *Aspergillus* and *Candida* species.

INTRODUCTION

Fungal Pathogens

Invasive fungal infections are well recognised as diseases of the immunocompromised host. Over the last twenty years there have been significant rises in the number of recorded instances of fungal infection (Groll et al., 1996, *J Infect* 33, 23-32). In part this is due to increased awareness and improved diagnosis of fungal infection. However, the primary cause of this increased incidence is the vast rise in the number of susceptible individuals. This is due to a number of factors including new and aggressive immunosuppressive therapies, increased survival in intensive care, increased numbers of transplant procedures and the greater use of antibiotics worldwide.

In certain patient groups, fungal infection occurs at high frequency; lung transplant recipients have a frequency of up to 20% colonisation and infection with a fungal organism and fungal infection in allogenic hoemopoetic stem transplant recipients is as high as 15% (Ribaud et al., 1999, *Clin Infect Dis.* 28:322-30).

Currently only four classes of antifungal drug are available to treat systemic fungal infections. These are the polyenes (e.g., amphotericin B), the azoles (e.g., ketoconazole or itraconazole) the echinocandins (e.g., caspofungin) and flucytosine.

The polyenes are the oldest class of antifungal agent being first introduced in the 1950s. The exact mode of action remains unclear but polyenes are only effective against organisms that contain sterols in their outer membranes. It has been proposed that amphotericin B interacts with membrane sterols to produce pores allowing leakage of cytoplasmic components and subsequent cell death.

Azoles function by the inhibition of 14α-demethylase via a cytochrome P450-dependent mechanism. This leads to a depletion of the membrane sterol ergosterol and the accumulation of sterol precursors resulting in a plasma membrane with altered fluidity and structure.

Echinocandins work by inhibiting the cell wall synthesis enzyme β-glucan synthase, leading to abnormal cell wall formation, osmotic sensitivity and cell lysis.

Flucytosine is a pyrimidine analogue interfering with cellular pyrimidine metabolism as well DNA, RNA and protein synthesis. However widespread resistance to flucyotosine limits its therapeutic use.

It can be seen that, to date, the currently available antifungal agents act primarily against only two cellular targets; membrane sterols (polyenes and azoles) and β-glucan synthase (echinocandins).

Resistance to both azoles and polyenes has been widely reported leaving only the recently introduced echinocandins to combat invasive fungal infections. As the use of echinocandins increases, resistance in fungi will inevitably occur.

The identification of new classes of antifungal agent with novel modes of action is therefore required to ensure positive therapeutic outcomes for patients in the future.

DHODH

Dihydroorotate dehydrogenase (DHODH; PyrE) is involved in the de novo synthesis of pyrimidines, catalysing the oxidation of dihydroorotate to orotate. Two classes of DHODH have been described on the basis of differences in amino acid sequence; Class II DHODH are found in most fungi (including *A. fumigatus* and *C. albicans*), animals, plants, gram-negative bacteria and archeabacteria. These use an FMN molecule as a cofactor, and, in the case of humans and fungi, this is recycled by means of oxidation via a quinone cofactor from the respiratory chain. The human and fungal proteins are non-covalently associated with the mitochondrial inner membrane by an N-terminal trans-membrane domain. The quinone-binding pocket is adjacent to, but distinct from the catalytic site of the enzyme. Class I enzymes are found in gram-positive bacteria, trypanosomes, *Saccharomyces cerevisiae*, and closely related fungi such as other members of the genus *Saccharomyces*.

A large number of inhibitors of human DHODH have been reported, including redoxal, brequinar, leflunomide, A771726, and atovaquone. In some cases, crystal structures for DHODH proteins complexed with inhibitors are available and structures of protein-inhibitor complexes are also available for rat and *P. falciparum* DHODH. The structures show that the inhibitors bind in the quinone pocket and are therefore assumed to function by preventing the cofactor from being reoxidised.

The distribution of class II DHODH across fungal species as been studied and, with the exception of certain *Saccharomyces* species, has been found in all fungi examined to date, with the evolutionary tree of the enzyme paralleling that of the organisms themselves. Thus, DHODH is present in pathogenic fungi such as *Aspergillus fumigatus, Candida albicans, Candida glabrata, Coccidioides immitis* and *Cryptococcus neoformans*. In those cases where genomic sequence is not available for particular pathogens, DHODH has been identified in related organisms with sequenced genomes, thereby indicating the presence of DHODH in *Blastomyces, Cladosporium* and *Scopulariopsis* species.

The inventors have optimised conditions for identifying inhibitors of DHODH suitable for use as antifungal agents.

SUMMARY OF THE INVENTION

The present invention relates to fungal DHODH as a target for antifungal therapy, in particular to conditions for optimally identifying inhibitors, e.g. small molecules, as potential antifungal compounds by determining whether a candidate agent is capable of inhibiting fungal DHODH activity.

Accordingly the invention provides the following:
a method of identifying an antifungal agent which targets a DHODH protein of a fungus comprising
(a) contacting a candidate substance with
  (i) a fungal DHODH protein; or
  (ii) a DHODH protein which comprises the sequence shown by SEQ ID NO:1 or 2; or
  (iii) a protein which has at least 50% identity with (ii) or (iii); or
  (iv) a protein comprising a variant and/or fragment of (ii), (iii) or (iv) which fragment has a length of at least 50 amino acids;
(b) under assay conditions of, optionally, 500 µM dihydroorotate, and/or 50 µM quinone, and/or 100 µM 2,6-dichloroindophenol, and/or at a DHODH enzyme concentration such that the enzyme activity is in a linear range with respect to time and protein concentration, and/or at pH 8.0, and/or in 150 mM NaCl, and/or in 50 mM Tris.HCl, and/or with 1% v/v DMSO, and/or with 8% v/v glycerol, and/or with 0.08% v/v Trition X-100, and/or incubated at room temperature, and/or incubated for 20-40 minutes, and/or where the assay has a Z' value of 0.375, and/or where the assay has a % CV value of <5% for minus-enzyme or completely-inhibited control; and,
(c) determining whether the candidate substance binds or modulates (i), (ii), (iii) or (iv), wherein binding or modulation of (i), (ii), (iii) or (iv) indicates that the candidate substance is an antifungal agent,
use of (i), (ii), (iii) or (iv) as defined above to identify or obtain an antifungal agent,
use of a counter-screen with
  (i) a mammalian DHODH protein which comprises the sequence shown by SEQ ID NO: 11; or
  (ii) a protein which has at least 80% identity with (i); or
  (iii), a protein comprising a variant and/or fragment of (i) or (ii) which fragment has a length of at least 50 amino acids;
such that the antifungal agents identified above are contacted with a mammalian DHODH to identify those which show little or no binding or modulation of the mammalian enzyme,
a compound identified by the above methods which impairs fungal DHODH function for use as an antifungal compound.
use of an antifungal agent identified by the method of the invention in the manufacture of a medicament for prevention or treatment of fungal infection, and
a method for preventing or treating a fungal infection comprising administering an antifungal agent identified by the screening method of the invention.

The method of the invention has identified a particular group of DHODH inhibitors. These inhibitors are the quinazolinone derivatives of formula (I) and pharmaceutically acceptable salts thereof:

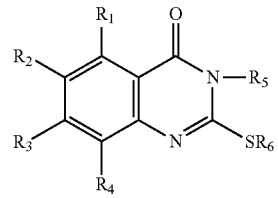

wherein:
R1 to R4 are each independently selected from H, F, Cl or the unsubstituted or substituted groups C1-C4 alkyl, C2-C4 alkenyl, OR', NR'R", cyano, —COR', —CO$_2$R', —CONR'R", —OCOR', —NR'COR" and —OCONR'R", wherein R' and R" are independently selected from hydrogen and C1-C4 alkyl;
R5 is unsubstituted or substituted phenyl; and
R6 is C1-C4 alkyl.

The invention therefore also provides pharmaceutical compositions comprising the quinazolinone derivatives of formula (I) or pharmaceutically acceptable salts thereof, and a pharmaceutically acceptable carrier or diluent; the quinazolinone derivatives of formula (I) or pharmaceutically acceptable salts thereof for use in the prevention or treatment of fungal infection; a method for preventing or treating a fungal infection comprising administering an effective amount of a quinazolinone derivative of formula (I) or a pharmaceutically acceptable salt thereof; and the use of the quinazolinone derivatives of formula (I) or pharmaceutically acceptable salts thereof in the manufacture of a medicament for the prevention or treatment of fungal infection.

Also provided is a DHODH inhibitor which is
2-Isopropylsulfanyl-3-(2-methoxy-phenyl)-7-methyl-3H-quinazolin-4-one,
2-Isopropylsulfanyl-3-(2-methoxy-phenyl)-6-methyl-3H-quinazolin-4-one,
2-Isopropylsulfanyl-3-(2-methoxy-phenyl)-5-methyl-3H-quinazolin-4-one,
2-Isopropylsulfanyl-5-methoxy-3-(2-methoxy-phenyl)-3H-quinazolin-4-one,
2-Ethylsulfanyl-3-(2-methoxy-phenyl)-7-methyl-3H-quinazolin-4-one,
6-Dimethylamino-2-isopropylsulfanyl-3-(2-methoxy-phenyl)-3H-quinazolin-4-one,
2-Isopropylsulfanyl-3-(2-methoxy-phenyl)-3H-quinazolin-4-one,
3-(2-Isopropyl-phenyl)-2-isopropylsulfanyl-3H-quinazolin-4-one,
3-(2-Ethyl-phenyl)-2-isopropylsulfanyl-3H-quinazolin-4-one,
2-Isopropylsulfanyl-6-methoxy-3-(2-methoxy-phenyl)-3H-quinazolin-4-one,
3-(2-Dimethylamino-phenyl)-2-isopropylsulfanyl-3H-quinazolin-4-one,
2-Ethylsulfanyl-5-methoxy-3-(2-methoxy-phenyl)-3H-quinazolin-4-one,
3-(2-Ethyl-phenyl)-2-ethylsulfanyl-3H-quinazolin-4-one,
2-Ethylsulfanyl-3-(2-methoxy-phenyl)-5-methyl-3H-quinazolin-4-one, or
2-Ethylsulfanyl-3-(2-isopropyl-phenyl)-3H-quinazolin-4-one,
or a pharmaceutically acceptable salt thereof.

DETAILED DESCRIPTION OF THE INVENTION

As mentioned above the invention relates to use of particular protein sequences (termed "proteins of the invention" herein) which are of, or derived from, fungal DHODH proteins (including homologues and/or fragments of the fungal DHODH proteins) to identify antifungal agents. The methods of the invention provide assays to screen compounds as potential antifungal compounds.

As used herein, a C1-C4 alkyl group or moiety can be linear or branched. Suitable such alkyl groups and moieties include methyl, ethyl, n-propyl, i-propyl, n-butyl, sec-butyl and tert-butyl.

As used herein, a C2-C4 alkenyl group or moiety can be linear or branched but is preferably linear. It contains one or more carbon-carbon double bonds. It is preferably a C2-C3 alkenyl group. Suitable such alkenyl groups and moieties include vinyl, allyl, propenyl and butenyl.

An alkyl or alkenyl group can be substituted or unsubstituted. Typically, it carries up to three substituents, e.g. one or two substituents. Suitable substituents are preferably themselves unsubstituted and include F, Cl, OH and O(C1-C4 alkyl). More preferably, an alkyl or alkenyl group is unsubstituted.

As used herein, the term DHODH may be defined as an enzyme which is capable of catalysing the oxidation of dihydroorotate. The DHODHs of the invention fall within classification EC 1.3.3.1 of the enzyme commission.

As used herein, the term antifungal agent may be defined as an agent that retards, destroys or prevents the growth of fungi, an agent used to treat fungal infections, or an agent that selectively eliminates fungal pathogens from a host with minimal toxicity to the host. The antifungal efficacy of a compound may be measured in vitro, e.g. with cultures fungi, or in vivo, e.g. in an infected host.

A protein of the invention (or a fungal DHODH protein) may be defined by similarity in sequence to another member of the family. As mentioned above this similarity may be based on percentage identity (for example to the sequences SEQ ID No. 1, 2 or 11).

The protein of the invention may be in isolated form (such as non-cellular form), for example when used in the method of the invention. Preferably, the isolated protein comprises a DHODH protein. The protein may comprise native, synthetic or recombinant protein. The protein may comprise combinations of native, synthetic or recombinant protein. The proteins of the invention may have a sequence which is the same as, or different from, naturally occurring DHODH proteins.

It is to be understood that the term "isolated from" may be read as "of" herein. Therefore references to proteins being "isolated from" a particular organism include proteins which were prepared by means other than obtaining them from the organism, such as synthetically or recombinantly.

Preferably, the protein of the invention is isolated from a fungus, more preferably a filamentous fungus, even more preferably an Ascomycete.

Preferably, the protein of the invention is isolated from an organism independently selected from the genera *Absidia; Acremonium; Alternaria; Aspergillus; Bipolaris;* Blastomyces; *Blumeria; Candida; Cladosporium; Coccidioides; Colletotrichium; Cryptococcus; Curvularia; Encephalitozoon; Epicoccum; Epidermophyton; Exophiala; Exserohilum; Fonsecaea; Fusarium; Histoplasma; Leptosphaeria; Microsporum; Mycosphaerella; Neurospora, Paecilomyces; Paracoccidioides; Penicillium; Phialophora; Phytophthora; Plasmopara; Pneumocystis; Pseudallescheria; Pyricularia; Pythium; Puccinia; Rhizoctonia; Rhizomucor; Rhizopus; Saccharomyces; Scedosporium; Scopulariopsis; Sporothrix; Trichophyton; Trichosporon; Ustilago* and *Wangiella*.

Preferably, the protein of the invention is isolated from an organism selected from the species *Absidia corymbifera; Acremonium* spp.: *Alternaria alternata; Aspergillus flavus; Aspergillus fumigatus; Aspergillus nidulans; Aspergillus niger; Aspergillus parasiticus; Aspergillus terreus; Bipolaris* spp.; *Blastomyces dermatitidis; Blumeria graminis; Candida albicans; Candida glabrata; Candida krusei; Candida parapsilosis; Candida tropicalis; Cladosporium carrionii; Cladosporium cladosporoides; Cladosporium herbarium; Coccidioides immitis; Coccidioides posadasii; Curvularia lunata; Colletotrichium trifolii; Cryptococcus neoformans; Encephalitozoon cuniculi; Epicoccum nigrum; Epidermophyton floccosum; Exophiala* spp.: *Exserohilum rostratum; Fonsecaea pedrosoi; Fusarium graminarium; Fusarium solani; Fusarium sporotrichoides; Histoplasma capsulatum; Leptosphaeria nodorum; Microsporum canis; Mycosphaerella graminicola; Paecilomyces lilanicus; Paecilomyces varioti; Paracoccidioides brasiliensis; Penicillium chrysogenum; Phialophora verrucosa; Phytophthora capsici; Phytophthora infestans; Plasmopara viticola; Pneumocystis jiroveci; Puccinia coronata; Puccinia graminis; Pyricularia oryzae; Pythium ultimum; Rhizoctonia solani; Rhizomucor* spp.: *Rhizopus* spp.: *Saccharomyces* spp.; *Scedosporium apiospermum; Scedosporium prolificans; Scopulariopsis brevicaulis; Sporothrix* spp.; *Trichophyton mentagrophytes; Trichophyton interdigitale; Trichophyton rubrum; Trichosporon asahii; Trichosporon beigelii* and *Ustilago maydis*.

Variants of the above mentioned proteins of the invention are also provided, and are discussed below.

Preferably, the protein of the invention comprises substantially the protein sequences SEQ ID Nos. 1 or 2 or a variant thereof.

By the term "recombinant protein", is meant an amino acid or protein which has been produced using recombinant DNA or protein technology or methodologies which are known to the skilled technician.

The term "variant", and the terms "substantially the protein sequence" are used herein to refer to related sequences. As discussed below such related sequences are typically homologous to (share percentage identity with) a given sequence, for example over the entire length of the sequence or over a portion of a given length. The related sequence may also be a fragment of the sequence or of a homologous sequence.

By the term "variant", and the terms "substantially the protein sequence", we mean that the sequence has at least 50%, preferably 60%, more preferably 70%, and even more preferably, 80% sequence identity with the amino acid/protein sequences of any one of the sequences referred to. A sequence which is "substantially the protein sequence" may be the same as the relevant sequence.

An amino acid/protein sequence with a greater identity than 65% to any of the sequences referred to is also envisaged. An amino acid/protein sequence with a greater identity than 70% to any of the sequences referred to is also envisaged. An amino acid/protein sequence with a greater identity than 75% to any of the sequences referred to is also envisaged. An amino acid/protein sequence with a greater identity than 80% to any of the sequences referred to is also envisaged. Preferably, the amino acid/protein sequence has 85% identity with any of the sequences referred to, more preferably 90% identity, even more preferably 92% identity, even more preferably 95% identity, even more preferably 97% identity, even more preferably 98% identity and, most preferably, 99% identity with any of the referred to sequences.

The above mentioned percentage identities may be measured over the entire length of the original sequence or over a region of 15, 20, 50 or 100 amino acids of the original sequence. In a preferred embodiment percentage identity is measured with reference to SEQ ID Nos. 1, 2 or 11. Preferably the variant protein has at least 40% identity, such as at least 60% or at least 80% identity with SEQ ID Nos. 1, 2 or 11 or a portion of SEQ ID Nos. 1, 2 or 11.

Other suitable variants are those having homologous nucleotide sequences but comprising all, or portions of, sequence which are altered by the substitution of different codons that encode an amino acid with a side chain of similar biophysical properties to the amino acid it substitutes, to produce a conservative change. For example small non-polar, hydrophobic amino acids include glycine, alanine, leucine, isoleucine, valine, proline, and methionine. Large non-polar, hydrophobic amino acids include phenylalanine, tryptophan and tyrosine. The polar neutral amino acids include serine, threonine, cysteine, asparagine and glutamine. The positively charged (basic) amino acids include lysine, arginine and histidine. The negatively charged (acidic) amino acids include aspartic acid and glutamic acid. Certain organisms, including *Candida* are known to use non-standard codons compared to those used in the majority of eukaryotes. Any comparisons of proteins from such organisms with the sequences given here should take these differences into account.

Other modifications in protein sequences are also envisaged and within the scope of the claimed invention, i.e. those which occur during or after translation, e.g. by acetylation, amidation, carboxylation, phosphorylation, proteolytic cleavage or linkage to a ligand.

The protein of the invention may be used as a fusion protein, which is defined as a DHODH polypeptide or fragment thereof fused via a covalent bond (e.g. a peptide bond), at optionally the N-terminus or the C-terminus, to an amino acid sequence of another protein (or portion thereof; preferably at least a 10, 20 or 50 amino acid portion of the protein).

The term "variant", and the terms "substantially the protein sequence" also include a fragment of the relevant protein sequences, including a fragment of the homologous sequences (which have percentage identity to a specified sequence) referred to above. A protein fragment will typically comprise at least 10 amino acids, such as at least 20, 30, 50, 80, 100, 150, 200, 300, 400 or 500 amino acids. The fragments may lack at least 3 amino acids, such as at least 10, 20, 30, 40, 50, 60, 70, 80, 90, 100 or 110 amino acids from either or both ends of the protein. In one embodiment of the invention, the protein of the invention is a DHODH fragment truncated at the N-terminus to remove the mitochondrial targetting sequence and the transmembrane region of DHODH. These may be determined by using publicly available software such as TMHMM, PSORTII or MitoProtII, or, in the case of transmembrane regions, by eye, e.g., 15-20 consecutive hydrophobic residues.

The invention provides a method of screening which may be used to identify modulators of DHODH proteins, such as inhibitors of activity of the proteins of the invention. In one embodiment of the method a candidate substance is contacted with a protein of the invention and whether or not the candidate substance binds or modulates the protein is determined.

The modulator may promote (agonise) or inhibit (antagonise) the activity of the protein. A therapeutic modulator (against fungal infection) will inhibit the activity of the protein of the invention.

The method may be carried out in vitro (inside or outside a cell) or in vivo, for example on a cell, cell culture or cell extract. The cell may or may not be a cell in which the polynucleotide or protein is naturally present. The cell may or may not be a fungal cell, or may or may not be a cell of any of the fungi mentioned herein. The protein may be present in a non-cellular form in the method, thus the protein may be in the form of a recombinant protein purified from a cell.

Whether or not a candidate substance modulates the activity of the protein may be determined by providing the candidate substance to the protein under conditions that permit activity of the protein, and determining whether the candidate substance is able to modulate the activity of the protein. Alternatively, binding of a candidate substance to the protein may be measured. The binding may be determined by measuring a characteristic of the protein that changes upon binding, such as spectroscopic changes.

The activity which is measured may be any of the activities of the protein of the invention mentioned herein, such as DHODH activity. In one embodiment the screening method comprises carrying out a DHODH reaction in the presence and absence of the candidate substance to determine whether the candidate substance inhibits the DHODH activity of the protein of the invention, wherein the DHODH reaction is carried out by contacting said protein with dihydroorotate, under conditions in which in the absence of the candidate substance the protein catalyses oxidation of the dihydroorotate.

In a preferred embodiment the inhibition of the DHODH reaction is measured by addition of quinone and 2,6-dichloroindophenol (DCIP), and detecting the reduction of 2,6-dichloroindophenol spectroscopically at 600 nm. A range of quinones are known and may be suitable, including 1,4-benzoquinone ($Q_0$), ubiquinone 30 ($Q_6$), ubiquinone 50 ($Q_{10}$), decylubiquinone ($Q_D$), ubiquinone 5 (coenzyme Q1), ubiquinone 10 (coenzyme Q2) and ubiquinone 20 (coenzyme Q4). Other suitable electron acceptors may be used instead of DCIP and assays may be carried out in the absence of quinone. In another embodiment of the invention, the oxidation of DHO may be measured directly and spectrophotometrically, for instance at 277 or 296 nm.

In one embodiment of the assay, the concentration of dihydroorotate of is between 100 and 2000 µM, preferably between 200 and 1000 µM, more preferably 500 µM; The quinone concentration is between 25 and 100 µM, preferably between 40 and 60 µM, more preferably 50 µM; The concentration of 2,6-dichloroindophenol is between 20 and 400 µM, preferably between 50 and 200 µM, more preferably 100 µM; The pH is between 7.0 and 9.0, preferably between 7.5 and 8.5, more preferably 8.0; The NaCl or KCl concentration is between 75 and 300 mM, preferably between 100 and 200 mM, more preferably 150 mM; The Tris.HCl concentration is between 10 and 200 mM, preferably between 25 and 100 mM, more preferably 50 mM; The DMSO concentration is between 0 and 5% v/v, preferably between 0.25 and 3%, even more preferably between 0.5 and 2%, most preferably 1%; The glycerol concentration is between 0 and 20% v/v, preferably between 1 and 10%, most preferably 8%; The Triton X-100 concentration is between 0 and 5% v/v, preferably between 0.25 and 2%, most preferably 0.08%; The reaction temperature is between 10 and 37° C., preferably between 15 and 25° C., more preferably room temperature; The Z' value is ≥0.2, preferably ≥0.3, preferably ≥0.375, more preferably ≥0.4, even more preferably ≥0.5, most preferably ≥0.6; The % CV value is <10%, preferably <7.5%, more preferably <5%, even more preferably <3%.

In an embodiment of the invention, the concentration of the enzyme is one that is in the linear range with respect to time and protein concentration, i.e., reaction incubation time and concentration of DHODH enzyme are chosen such the time is in the linear phase of the plot of product production against time, and such that there is a direct and linear relationship between the amount of enzyme and the amount of product produced. Preferably the incubation time is between 10 and 60 minutes, more preferably between 20 and 40 minutes.

The parameters % CV, the coefficient of variation, and Z', the dynamic range, are defined as follows, where SD stands for standard deviation; 100% control, a microwell plate where all wells contain the uninhibited reaction; 0% control, a microwell plate where all wells contain a completely inhibited reaction, or no enzyme:

% CV=(Standard deviation of data from whole plate/ mean of data from whole plate)×100, where the plate is a 0% control.

Z'=1−((3SD 100% control+3SD 0% control)/(mean 0% control−mean 100% control))

In one embodiment of the invention, compounds screened against a fungal DHODH are used in a counter-screen with a mammalian DHODH protein, which comprises the sequence shown by SEQ ID NO: 11; or a protein which has at least 80% identity with mammalian DHODH; or a protein comprising a fragment or variant of the mammalian DHODH, which fragment has a length of at least 50 amino acids, such that the antifungal agents identified above are contacted with a mammalian DHODH to identify those which show little or no binding or modulation of the human enzyme.

In one embodiment the method is capable of identifying inhibitors that have an IC 50 (concentration of inhibitor that inhibits enzyme activity by 50%) of 10 nM to 100 nM or 20 nM to 100 nM. In another embodiment the method is capable of identifying inhibitors that have a Ki of 20 nM to 60 nm. The method may be capable of identifying inhibitors that have a binding to DHODH which is reversible and/or competitive with coenzyme Q cosubstrate (indicating binding of the inhibitor within the quinone pocket of DHODH). Thus the inhibitor may be selected based on possessing one or more of these physical properties.

For the DHODH enzyme of *A. fumigatus*, the following regions contribute to the quinone pocket environment:
Valine 87 to glutamic acid 135
Valine 144 to leucine 218
Asparagine 487 to arginine 530.

For the DHODH enzyme of *C. albicans*, the following regions contribute to the quinone pocket environment:
Tyrosine 52 to leucine 95
Valine 106 to serine 180
Asparagine 388 to glutamic acid 431.

Thus the inhibitor may selected based on its ability to bind any of these regions of the DHODH enzyme of *A. fumigatus* or *C. albicans* or to equivalent regions of other DHODH enzymes.

Suitable candidate substances which can tested in the above methods include antibody products (for example, monoclonal and polyclonal antibodies, single chain antibodies, chimeric antibodies and CDR-grafted antibodies). Furthermore, combinatorial libraries, defined chemical identities, peptide and peptide mimetics, oligonucleotides and natural product libraries, such as display libraries (e.g. phage display libraries) may also be tested. The candidate substances may be chemical compounds. Batches of the candidate substances may be used in an initial screen of, for example, ten substances per reaction, and the substances from batches which show inhibition tested individually.

According to a further aspect of the present invention, there is provided use of a protein of the invention for the preparation of a medicament for the treatment of a fungal infection.

The protein of the invention may be modified prior to use, preferably to produce a derivative or variant thereof. The protein may be derivatised. The protein may not be modified or derivatised.

Preferably, the medicament is adapted to retard or prevent a fungal infection. The treatment may comprise retarding or preventing fungal infection. Preferably, the drug and/or medicament comprises an inhibitor, preferably a DHODH inhibitor. Preferably, the drug or medicament is adapted to inhibit function of the protein or a fragment thereof.

The method of the invention has been used to identify compounds which target a DHODH protein of a fungus. By this method, the inventors identified the quinazolinone compounds of formula (I) as DHODH inhibitors. These compounds have been subsequently assessed in anti-fungal assays and have been found to have anti-fungal activity against a number of strains of *Aspergillus* fungi.

The present invention accordingly provides the quinazolinone compounds of formula (I) and their pharmaceutically acceptable salts for use in the treatment or prevention of fungal infection. Other compounds similarly identified by the method of the invention can also be expected to have beneficial anti-fungal activity and may also therefore be used in the treatment or prevention of anti-fungal infection.

In the compounds of formula (I), R1 to R4 are preferably independently selected from H, C1-C4 alkyl, C2-C4 alkenyl, OR', NR'R", F, Cl and cyano, where R' and R" are independently H or C1-C4 alkyl. More preferably, R1 to R4 are independently selected from H, C1-C4 alkyl, OR' and NR'R", where R' and R" are independently H or C1-C4 alkyl, preferably H or C1-C2 alkyl. Most preferably, R1 to R4 are independently selected from H, methyl, —OMe or —N(Me)$_2$.

R1 to R4 may themselves be unsubstituted or substituted. Where R1 to R4 are substituted, they typically carry one, two or three, preferably one, substituent which is itself unsubstituted.

Suitable substituents include F, Cl, OH and O(C1-C4 alkyl). More preferably, R1 to R4 are unsubstituted.

The substituents on the R5 phenyl ring are typically chosen from the groups defined as R1 to R4 above. Preferred substituents are C1-C4 alkyl, C2-C4 alkenyl, OR', NR'R", F, Cl and cyano, where R' and R" are independently H or C1-C4 alkyl. More preferred substituents are C1-C4 alkyl, OR' or NR'R", where R' and R" are independently H or C1-C2 alkyl. Typically, the R5 phenyl ring is unsubstituted or carries one or two substituents. One substituent is preferred.

The substituents on the R5 phenyl ring may be unsubstituted or substituted. Typically they are unsubstituted or substituted with from one to three, preferably one, substituent which is itself unsubstituted. Suitable substituents include F, Cl, OH and O(C1-C4 alkyl). More preferably, the substituents on the R5 phenyl ring are unsubstituted.

R6 is preferably ethyl or isopropyl, most preferably isopropyl.

Particular examples of quinazolinone compounds of the invention are the compounds identified as Compound Examples 1 to 15 in Example 3, and their pharmaceutically acceptable salts.

Compounds containing one or more chiral centre may be used in enantiomerically or diastereoisomerically pure form, or in the form of a mixture of isomers. For the avoidance of doubt, the compounds can, if desired, be used in the form of solvates. Further, for the avoidance of doubt, the compounds may be used in any tautomeric form.

As used herein, a pharmaceutically acceptable salt is a salt with a pharmaceutically acceptable acid or base. Pharmaceutically acceptable acids include both inorganic acids such as hydrochloric, sulphuric, phosphoric, diphosphoric, hydrobromic, hydroiodic or nitric acid and organic acids such as citric, fumaric, maleic, malic, ascorbic, succinic, tartaric, benzoic, acetic, methanesulphonic, ethanesulphonic, benzenesulphonic, p-toluenesulphonic acid, formic, acetic, propionic, glycolic, lactic, pyruvic, oxalic, salicylic, trichloroacetic, picric, trifluoroacetic, cinnamic, pamoic, malonic, mandelic, bismethylene salicylic, ethanedisulfonic, gluconic, citraconic, aspartic, stearic, palmitic, EDTA, p-aminobenzoic or glutamic acid, sulfates, nitrates, phosphates, perchlorates, borates, acetates, benzoates, hydroxynaphthoates, glycerophosphates or ketoglutarates. Further examples of pharmaceutically acceptable inorganic or organic acid addition salts include the pharmaceutically acceptable salts listed in Journal of Pharmaceutical Science, 66, 2 (1977) which are known to the skilled artisan. Pharmaceutically acceptable bases include alkali metal (e.g. sodium or potassium) and alkali earth metal (e.g. calcium or magnesium) hydroxides and organic bases such as alkyl amines, aralkyl amines and heterocyclic amines, lysine, guanidine, diethanolamine and choline.

Also intended as pharmaceutically acceptable acid addition salts are the hydrates which the quinazolinone compounds are able to form.

The acid addition salts may be obtained as the direct products of compound synthesis. In the alternative, the free base may be dissolved in a suitable solvent containing the appropriate acid, and the salt isolated by evaporating the solvent or otherwise separating the salt and solvent.

The solvates may be obtained using standard low molecular weight solvents according to methods known to the skilled artisan.

The quinazolinone derivatives may also be used in the form of a prodrug. A prodrug is an analogue of a compound of the invention which will be converted in vivo to the desired active compound. Examples of suitable prodrugs include compounds of formula (I) which have been modified at a carboxylic acid group to form an ester, or at hydroxyl group to form an ester or carbamate. Other suitable methods will be known to those skilled in the art. Further suitable prodrugs include those in which a nitrogen atom of a compound of formula (I) is quaternised by addition of an ester or alkyl ester group. For example, the nitrogen atom of an amine group at R1 to R4 or on a substituent of the R5 phenyl ring may be quaternised by addition of a —CH$_2$—O—COR group, wherein R is typically methyl or tert-butyl.

The quinazolinone derivatives of formula (I) can be prepared as follows:

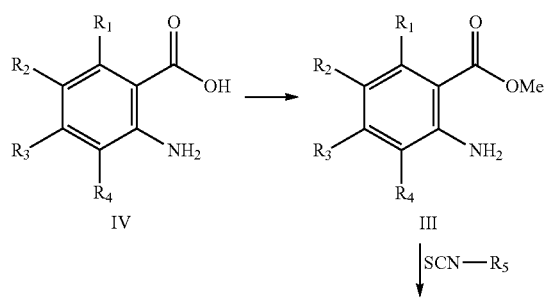

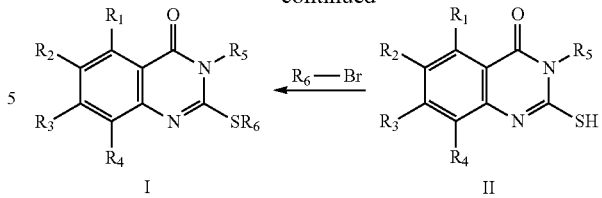

In a first step, the 2-amino benzoic acid compound (IV) is esterified, for example in methanol and concentrated sulfuric acid. In an alternative process, the 2-nitro benzoic acid may be used and, following esterification, the nitro group converted to an amino group in appropriate reducing conditions such as Raney Nickel in methanol. Further details of the synthesis of the compounds of the invention can be found in Example 3. The starting materials for the above synthesis are commercially available or could be prepared by a skilled chemist using known techniques.

As discussed above, the quinazolinone compounds of formula (I), and other compounds identified by the method of the invention, are useful in the treatment or prevention of fungal infection. Preferably, the fungal infection comprises an infection by a fungus, more preferably an Ascomycete, and even more preferably, an organism selected from the genera *Absidia; Acremonium; Alternaria; Aspergillus; Bipolaris; Blastomyces; Blumeria; Candida; Cladosporium; Coccidioides; Colletotrichium; Cryptococcus; Curvularia; Encephalitozoon; Epicoccum; Epidermophyton; Exophiala; Exserohilum; Fonsecaea; Fusarium; Histoplasma; Leptosphaeria; Microsporum; Mycosphaerella; Neurospora, Paecilomyces; Paracoccidioides; Penicillium; Phialophora; Phytophthora; Plasmopara; Pneumocystis; Pseudallescheria; Pyricularia; Pythium; Puccinia; Rhizoctonia; Rhizomucor; Rhizopus; Saccharomyces; Scedosporium; Scopulariopsis; Sporothrix; Trichophyton; Trichosporon; Ustilago* and *Wangiella.*

Preferably, the fungal infection comprises an infection by an organism selected from the species *Absidia corymbifera; Acremonium* spp.: *Alternaria alternata; Aspergillus flavus; Aspergillus fumigatus; Aspergillus nidulans; Aspergillus niger; Aspergillus parasiticus; Aspergillus terreus; Bipolaris* spp.: *Blastomyces dermatitidis; Blunzeria graminis; Candida albicans; Candida glabrata; Candida krusei; Candida parapsilosis; Candida tropicalis; Cladosporium carrionii; Cladosporium cladosporoides; Cladosporium herbarium; Coccidioides immitis; Coccidioides posadasii; Curvularia lunata; Colletotrichium trifolii; Cryptococcus neoformans; Encephalitozoon cuniculi; Epicoccum nigrunz; Epidermophyton floccosum; Exophiala* spp.: *Exserohilum rostratum; Fonsecaea pedrosoi; Fusarium graminarium; Fusarium solani; Fusarium sporotrichoides; Histoplasma capsulatum; Leptosphaeria nodosum; Microsporum canis; Mycosphaerella graminicola; Paecilomyces lilanicus; Paecilomyces varioti; Paracoccidioides brasiliensis; Penicillium chrysogenum; Phialophora verrucosa; Phytophthora capsici; Phytophthora infestans; Plasmopara viticola; Pneumocystis jiroveci; Puccinia coronata; Puccinia graminis; Pyricularia ozyzae; Pythium ultimum; Rhizoctonia solani; Rhizomucor* spp.: *Rhizopus* spp.: *Saccharomyces* spp.; *Scedosporium apiospermum; Scedosporium prolificans; Scopulariopsis brevicaulis; Sporothrix* spp.; *Trichophyton mentagrophytes; Trichophyton interdigitale; Trichophyton rubrunz; Trichosporon asahii; Trichosporon beigelii* and *Ustilago nzaydis.*

In one embodiment, the fungal infection is by an organism of the *Aspergillus* genus, for example by *Aspergillus flavus;*

*Aspergillus fumigatus; Aspergillus nidulans; Aspergillus niger; Aspergillus parasiticus;* or *Aspergillus terreus.*

Examples of fungal diseases, which can be prevented or treated using the compounds of the invention, include both systemic and superficial infections. The fungal diseases include invasive fungal diseases caused by *Aspergillus* and *Candida* species such as aspergillosis or candidiasis, but also local forms of these infections. The compounds of the invention are particularly useful against diseases caused by *Aspergillus* species, for which a fungicidal drug is required which has lower toxicity than amphotericin. The invention also provides for the treatment of dermatological infections.

Examples of systemic infections which might be prevented or treated using the compounds of the invention include: systemic candidiasis; pulmonary aspergillosis, e.g. in immunosuppressed patients such as bone marrow recipients or AIDS patients; systemic aspergillosis; cryptococcal meningitis; rhinocerebral mucomycosis; blastomycosis; histoplasmosis; coccidiomycosis; paracoccidiomycosis; lobomycosis; sporotrichosis; chromoblastomycosis; phaeohyphomycosis; zygomycosis; cryptococcosis and disseminated sporotrichosis.

Examples of superficial infections, which can be prevented or treated using the compounds of the invention, include: ring worm; athlete's foot; tinea unguium (nail infection); candidiasis of skin, mouth or vagina; and chronic mucocutaneous candidiasis.

Examples of diseases or conditions which are caused by fungi or where fungi exacerbate an allergic response, and which can be prevented or treated using the compounds of the invention, include allergic bronchopulmonary asthma (ABPA); asthma, rhinosinusitis and sinusitis.

In order to use DHODH inhibitors, for example the quinazolinone derivatives of formula (I) or their pharmaceutically acceptable salts, in therapy (human or veterinary), they will normally be formulated into a pharmaceutical composition in accordance with standard pharmaceutical practice, e. g. by admixing the DHODH inhibitor and a pharmaceutically acceptable carrier.

Thus according to a further aspect of the invention there is provided a pharmaceutical composition comprising a DHODH inhibitor, for example a quinazolinone derivative of formula (I) or a pharmaceutically acceptable salt thereof, and a pharmaceutically acceptable carrier. The pharmaceutical compositions are particularly useful in the prevention or treatment of fungal infections, preferably, in the treatment of *Aspergillus* or *Candida* fungal infections.

The pharmaceutical composition typically contains up to 85 wt % of a DHODH inhibitor, for example a quinazolinone derivative of formula (I) or a pharmaceutically acceptable salt thereof. More typically, it contains up to 50 wt % of a DHODH inhibitor, for example a quinazolinone derivative of formula (I) or a pharmaceutically acceptable salt thereof. Preferred pharmaceutical compositions are sterile and pyrogen free. Where a DHODH inhibitor, for example a quinazolinone derivative of formula (I) or a pharmaceutically acceptable salt thereof, can exist as optical isomers, the pharmaceutical compositions provided by the invention typically contain a substantially pure optical isomer.

DHODH inhibitors such as the quinazolinone derivatives of formula (I) or pharmaceutically acceptable salts thereof may be administered to a host by any of the routes conventionally used for drug administration, for example they may be administered parenterally, orally, topically (including buccal, sublingual or transdermal) or by inhalation. The most suitable route for administration in any given case will depend on the particular DHODH inhibitor, the infectious organism involved, the host, and the nature and severity of the disease and the physical condition of the host.

As discussed above, the DHODH inhibitors such as the quinazolinone derivatives of formula (I) or pharmaceutically acceptable salts thereof, are typically formulated for administration with a pharmaceutically acceptable carrier or diluent. For example, solid oral forms may contain, together with the active compound, solubilising agents, e.g. cyclodextrins or modified cyclodextrins; diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Such pharmaceutical preparations may be manufactured in known manner, for example, by means of mixing, granulating, tabletting, sugar-coating, or film coating processes.

Liquid dispersions for oral administration may be solutions, syrups, emulsions and suspensions. The solutions may contain solubilising agents e.g. cyclodextrins or modified cyclodextrins. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspensions or solutions for intramuscular injections may contain, together with the active compound, a pharmaceutically acceptable carrier, e.g. sterile water, olive oil, ethyl oleate, glycols, e.g. propylene glycol; solubilising agents, e.g. cyclodextrins or modified cyclodextrins, and if desired, a suitable amount of lidocaine hydrochloride.

Solutions for intravenous or infusions may contain as carrier, for example, sterile water and solubilising agents, e.g. cyclodextrins or modified cyclodextrins or preferably they may be in the form of sterile, aqueous, isotonic saline solutions.

A therapeutically effective amount a DHODH inhibitor, for example a quinazolinone derivative of formula (I) or a pharmaceutically acceptable salt thereof, is administered to a patient. A typical daily dose is up to 200 mg per kg of body weight, for example from 0.001 to 200 mg per kg of body weight, according to the activity of the specific compound, the age, weight and conditions of the subject to be treated, the type and severity of the disease and the frequency and route of administration. Preferably, daily dosage levels are from 0.05 mg to 50 g, for example from 0.1 mg to 10 mg. The DHODH inhibitor, for example the quinazolinone derivative of formula (I) or pharmaceutically acceptable salt thereof, is typically administered to the patient in a non-toxic amount.

The DHODH inhibitors, for example the quinazolinone derivative of formula (I) or pharmaceutically acceptable salt thereof, may be administered in combination, e. g. simultaneously, sequentially or separately, with one or more other therapeutically active, e. g. antifungal, compounds.

All publications, including but not limited to patents and patent applications, cited in this specification are herein incorporated by reference as if each individual publication were specifically and individually indicated to be incorporated by reference herein as though fully set forth.

The following examples are to be construed as merely illustrative and not a limitation on the scope of the invention in any way.

EXAMPLES

Example 1

Preparation of Recombinant DHODH 1.1 Recombinant *A. Fumigatus* DHODH

An N-terminally truncated DHODH construct (AF_DHODH_TR) lacking the mitochondrial targeting sequence and the transmembrane domain was prepared, encoding a protein starting at alanine 89 (ATDTRA . . . ). RNA was prepared from *A. fumigatus* biomass using a FastRNA Pro Red kit from QBiogene and a Fastprep FP120 instrument following the manufacturers instructions. The RNA was DNase treated with Turbo DNAfree (Ambion) to remove contaminating DNA. cDNA was prepared from the DNase-treated RNA using AMV reverse transcriptase (Promega) following the manufacturers protocol.

Primers were designed to clone *A. fumigatus* DHODH cDNA into pET-30 (Novagen) by ligation independent cloning (LIC):

```
                                     SEQ ID No. 3
JO_AFpyrEtr_F4
GACGACGACAAGATGGCGACGGATACCAGGGCAAG SEQ ID No. 4
JO_AFpyrE_R3
GAGGAGAAGCCCGGTCTATTGACGGTTTTTCTTTTCC
```

High fidelity PCR of AF_DHODH_TR was carried out using KOD polymerase (Novagen), *A fumigatus* cDNA and primers JO_AFpyrEtr_F4 and JO_AFpyrE_R3. The PCR product was purified using a Qiaquick column (Qiagen) and treated with T4 DNA polymerase and dATP to produce overhangs for cloning into a LIC vector (Novagen). The treated DNA was then annealed to ready-prepared pET-30. The sample was transformed into competent NovaBlue *E. coli* (GigaSingles, Novagen). Plasmid DNA from transformants was sequenced to confirm the cDNA was correctly cloned.

pET-30_ AF_DHODH_TR was digested with KpnI and HindIII (Fermentas) to release the coding sequence of AF_DHODH_TR. pET43.1 vector DNA was also treated with KpnI and HindIII. The vector and insert were ligated together using T4 DNA ligase (Fermentas) in an overnight reaction at 14° C. A sample of the ligation reaction was transformed into electrocompetent Genehogs (Invitrogen) by electroporation. Transformants were obtained and plasmid DNA prepared. Diagnostic digests with EcoRV confirmed that AF_DHODH_TR had been cloned into pET43.1.

Protein expression was performed as follows: pET43.1_AF_DHODH_TR DNA was transformed into BL21 DE3 *E. coli* (Novagen) and the transformation mixture incubated in LB broth plus 100 ug/ml ampicillin overnight at 37° C. with shaking. 1 ml of the overnight culture was inoculated into 50 ml of LB ampicillin plus 1% glucose and flavin mononucleotide (final concentration 100 uM) and incubated at 37° C. with shaking until the OD600 was greater than 0.5. IPTG (final concentration 0.5 mM) was added and the cultures incubated at 18° C. with shaking overnight.

The culture was centrifuged at 4000 g for 20 min to pellet the *E coli*. A Bugbuster mix was prepared (1× Bugbuster, 25 U/ml Benzonase, 1 kU/ml rLysozyme (all Novagen), 1/100 vol of protease inhibitor cocktail for His-tagged proteins (Sigma) and 100 uM FMN) and 3-5 ml was added to the bacterial pellet. Following incubation at room temperature for 10-20 min with mixing a clear lysate was obtained. The lysate was centrifuged at 16000 g for 20 min at 4° C. Meanwhile 1 ml of Ni-NTA His-bind resin (Novagen) was washed with 5 ml of wash buffer (50 mM sodium phosphate pH8, 500 mM NaCl, 20 mM imidazole, 0.1% Tween 20) and pre-equilibrated with Bugbuster mix on ice. The lysate supernatant was mixed with the pre-equilibrated resin for 1-2 h on ice. The resin and lysate mixture was then poured into a 0.8×4 cm Poly-Prep chromatography column (Bio-Rad). The flow-through was collected. The resin was washed twice with 5 ml of wash buffer. The protein was eluted with 4×0.5 ml of elution buffer (50 mM sodium phosphate pH8, 500 mM NaCl, 250 mM imidazole, 0.1% Tween 20, 1/100 vol of protease inhibitor cocktail). The eluate was then subjected to buffer exchange using a PD10 column (GE Healthcare) and eluting in DHODH assay buffer (50 mM Tris-HCl pH8, 150 mM KCl, 10% glycerol, 0.1% triton X-100).

1.2 Recombinant DHODH from Human, *Candida Albicans* and Rat

The method for producing these proteins was the same as described above for AF_DHODH. In the case of human and rat, cDNA clones were obtained from Geneservice Ltd. The complete cDNA for human DHODH in pCMVsport6 was present in the IMAGE clone 6064723 (MGC70636) and bases 16-1188 of the *Rattus norvegicus* cDNA in pExpress I were present in the IMAGE clone 7317263. N-terminally truncated human DHODH was LIC cloned into pET30 and then sub-cloned into pET43.1 as described for AF_DHODH using the primers JO_hD licF2 and JO_hD licR1 listed below. N-terminally truncated rat DHODH was cloned directly into pET43.1 by LIC cloning using the primers JO_rD licF2 and JO_rD licR1 listed below. *Candida albicans* cDNA was prepared as for *A. fumigatus* cDNA described above. Due to differences in the genetic code for *C. albicans*, mutagenesis of two CTG codons to TCG codons was carried out by PCR mutagenesis followed by fusion PCR as described in Zameitat et al. 2006, FEBS Journal 273, 3183-3191. The mutated product was cloned into pGEMTeasy (Promega), sequenced and then subjected to LIC cloning into pET43.1 using the primers JO_CAD licF3 and JO_CAD licR1.

```
SEQ ID No. 5:
JO_hD licF2      GACGACGACAAGATGGCCACGGGAGATGAGCG

SEQ ID No. 6:
JO_hD licR1      GAGGAGAAGCCCGGTTCACCTCCGATGATCTGCTC

SEQ ID No. 7:
JO_rD licF2      GACGACGACAAGATGACGGCCACAGGGGATGAC

SEQ ID No. 8:
JO_rD licR1      GAGGAGAAGCCCGGTTCACCTCCGATGATCTGCTC

SEQ ID No. 9:
JO_CAD licF3     GACGACGACAAGATGTCAAGATCAGCAATCCATGA

SEQ ID No. 10:
JO_CAD licR1     GAGGAGAAGCCCGGTTCACTTATCATCAGAGCCAA
```

Following cloning into pET-43.1, the procedure outlined above for AF_DHODH was followed for the expression and purification of the recombinant proteins.

Example 2

High-Throughput Screen for DHODH Inhibitors

Screening was carried out using a Thermo Labsystems Multidrop 384 machine (Multidrop® 384), complete with dispensing cassette and plate adapter, and Tecan Genesis Freedom and Tecan Te-Mo automated liquid handling robots.

1. The following buffer and stock solution were prepared:

Buffer A: 62.5 mM TrisHCl (pH8.0), 150 mM NaCl, 10% v/v glycerol

DHO/Coenzyme Q2/DCIP solution: 19.848 mg dihydroorotate (DHO; Sigma) was dissolved in 160 µl DMSO. Coenzyme Q2 (Sigma) was dissolved in DMSO to give a concentration of 10 mg/ml. 7.236 mg 2,6-dichloroindophenol (DCIP; Sigma) was dissolved in 160 µl DMSO. The stock solution was made with 127.36 µl DHO, 127.36 µl DCIP and 318.4 µl Coenzyme Q2, made up to 80 ml with Buffer A. Final concentrations in assay wells were; DHO, 500 µM; Coenzyme Q, 50 µM; DCIP, 100 µM.

2. Compounds were aliquotted into 384-well microtitre plates at a range of dilutions to give final concentrations in the assay of 100-0.001 mM. Duplicate sets of plates were used such that one set received enzyme while a control set received no enzyme. Since compounds are frequently dissolved in DMSO or a DMSO/water mixture, assays were set up to give a final concentration of 1% (v/v) DMSO in wells.

3. Recombinant *A. fumigatus* DHODH was suspended in Buffer A to give a concentration of 1435.8 ng protein in 20 µl. Then 20 µl of DHODH solution was added to all the +enzyme plates and 20 µl of Buffer A was added to all the control –enzyme plates.

4. 20 µl of DHO/Coenzyme Q2/DCIP solution was added to all the wells, after which plates were incubated at room temperature for 24 minutes each and then read on a Tecan Safire spectrophotometer at 600 nm.

Recombinant DHODH from human or *C. albicans* was assayed in the same way. It is necessary to adjust the enzyme concentration and reaction time to take into account variations in activity of enzyme batches, thus the incubation time was 20 minutes for the *C. albicans* enzyme and 34 minutes for the human enzyme. Results are shown in Table 1. Measurements of assay quality are shown in Table 2. Compounds are screened against a fungal and human enzyme to identify compounds which are selective for the fungal enzyme. The inventors have also found that the assay can be carried out in a final concentration of 150 mM KCl as opposed to NaCl, and that addition of Triton X-100 can be of value under some circumstances.

TABLE 1

IC50 values for DHODH inhibitors identified from screens[1]

|  | Human | C. albicans | A. fumigatus |
| --- | --- | --- | --- |
| Brequinar | 0.0118 | 143.0 | n.d |
| Compound 1 | 8.6 | 36.1 | n.d. |
| Compound 2 | >128.0 | >128.0 | n.d. |
| Compound 3 | >133.2 | >133.2 | 2.14 |

[1]Values are IC50 in µM; n.d., not done.

TABLE 2

Assay quality measurements for DHODH high-throughput screens

|  | Human | C. albicans | A. fumigatus |
| --- | --- | --- | --- |
| Z'[1] | 0.375 | 0.625 | n.d. |
| % CV (0% control)[1] | 2.8% | 2.7% | n.d. |

[1]Parameters are defined in "Detailed Description of the Invention" above; n.d., not done.

Example 3

DHODH Inhibitors

The following compounds were identified by the method of the Example 2 as DHODH inhibitors. Results from the Example 2 screen, and details of the preparation of these compounds are also provided.

1. 2-Isopropylsulfanyl-3-(2-methoxy-phenyl)-7-methyl-3H-quinazolin-4-one,
2. 2-Isopropylsulfanyl-3-(2-methoxy-phenyl)-6-methyl-3H-quinazolin-4-one,
3. 2-Isopropylsulfanyl-3-(2-methoxy-phenyl)-5-methyl-3H-quinazolin-4-one,
4. 2-Isopropylsulfanyl-5-methoxy-3-(2-methoxy-phenyl)-3H-quinazolin-4-one,
5. 2-Ethylsulfanyl-3-(2-methoxy-phenyl)-7-methyl-3H-quinazolin-4-one,
6. 6-Dimethylamino-2-isopropylsulfanyl-3-(2-methoxy-phenyl)-3H-quinazolin-4-one,
7. 2-Isopropylsulfanyl-3-(2-methoxy-phenyl)-3H-quinazolin-4-one,
8. 3-(2-Isopropyl-phenyl)-2-isopropylsulfanyl-3H-quinazolin-4-one,
9. 3-(2-Ethyl-phenyl)-2-isopropylsulfanyl-3H-quinazolin-4-one,
10. 2-Isopropylsulfanyl-6-methoxy-3-(2-methoxy-phenyl)-3H-quinazolin-4-one,
11. 3-(2-Dimethylamino-phenyl)-2-isopropylsulfanyl-3H-quinazolin-4-one,
12. 2-Ethylsulfanyl-5-methoxy-3-(2-methoxy-phenyl)-3H-quinazolin-4-one,
13. 3-(2-Ethyl-phenyl)-2-ethylsulfanyl-3H-quinazolin-4-one,
14. 2-Ethylsulfanyl-3-(2-methoxy-phenyl)-5-methyl-3H-quinazolin-4-one,
15. 2-Ethylsulfanyl-3-(2-isopropyl-phenyl)-3H-quinazolin-4-one.

TABLE 3

IC50 values for Compound Examples 1 to 15 identified from screens[1]

| Compound Example | Human | C. albicans | A. fumigatus |
| --- | --- | --- | --- |
| 1 | 51.3 | 117 | 1.46 |
| 2 | 6.54 | 117 | 2.83 |
| 3 | 40.2 | 117 | 4.52 |
| 4 | 73 | 112 | 4.95 |
| 5 | 15.5 | 123 | 5.4 |
| 6 | 1.09 | 108 | 10.1 |
| 7 | 50.1 | 123 | 11.6 |
| 8 | 131 | 106 | 12.2 |
| 9 | 123 | 115 | 17.7 |
| 10 | 50.2 | 104 | 19.6 |
| 11 | 118 | 118 | 21.2 |
| 12 | 117 | 117 | 26.9 |
| 13 | 86.1 | 141 | 36.2 |
| 14 | 32.1 | 123 | 43.7 |
| 15 | 23.2 | 118 | 46.1 |

[1]Values are IC50 in µM.

Synthesis of Compound Examples 1 to 15

Reference Example 1

5-Dimethylamino-2-nitro-benzoic acid

Sodium cyanoborohydride (690 mg, 10.99 mmol) was added portion wise to a mixture of 5-amino-2-nitro benzoic acid (500 mg, 2.74 mmol) and formaldehyde (40% aqueous, 2.5 mL, 83.33 mmol) in acetonitrile (10 mL) and the mixture was stirred for 16 hr. Methanol (10 mL) was added and the reaction mixture was evaporated in vacuo to afford 5-dimethylamino-2-nitro-benzoic acid (900 mg, 89%) as brownish yellow solid.

Reference Example 2

2-Amino-4-methyl-benzoic acid methyl ester

Concentrated sulphuric acid (1 mL) was added to a solution of 2-amino-4-methyl-benzoic acid (1.0 g, 6.62 mmol) in dry methanol (10 mL) at 0° C., and then heated at reflux for 16 hr. The mixture was cooled to room temperature and concentrated in vacuo. The crude compound was diluted with water (25 mL) and basified with sodium bicarbonate (10 mL). The aqueous layer was extracted with ethyl acetate (2×50 mL) and the combined organic layers were washed with water (50 mL), brine (50 mL) and dried over sodium sulfate. The organic layer was concentrated under reduced pressure affording 2-amino-4-methyl-benzoic acid methyl ester (900 mg, 82%) as yellow liquid.

Reference Example 2a

The compound set out below was prepared in a manner analogous to Reference Example 2:

| Reference Example | Compound |
| --- | --- |
| 2a | 2-Amino-5-methoxy-benzoic acid methyl ester |

Reference Example 3

2-Amino-5-methyl-benzoic acid methyl ester

Thionyl chloride (2.88 mL, 39.69 mmol) was added drop wise to a solution of 2-amino-5-methyl-benzoic acid (3.0 g, 19.84 mmol) in methanol (10 mL) at 0° C. and refluxed for 16 hr. The reaction mixture was concentrated to dryness and the residue dissolved in chloroform (100 mL). The organic layer was washed with sodium bicarbonate solution (5×30 mL), water (3×30 mL), brine (3×30 mL) and dried over anhydrous sodium sulphate. The residue was concentrated under vacuum to yield the crude compound, which was purified by column chromatography over silica gel (100-200 mesh) using 2% ethyl acetate in pet ether as eluent to afford 2-amino-5-methyl-benzoic acid methyl ester (2.0 g, 61%) as a pale yellow semi solid.

Reference Example 3a to 3c

The compounds set out below were prepared in a manner analogous to Reference Example 3:

| Reference Example | Compound |
| --- | --- |
| 3a | 2-Amino-6-methyl-benzoic acid methyl ester |
| 3b | 2-Amino-6-methoxy-benzoic acid methyl ester |
| 3c | 5-Dimethylamino-2-nitro-benzoic acid methyl ester |

Reference Example 4

2-Amino-5-dimethylamino-benzoic acid methyl ester

Raney Nickel (80 mg) was added to a suspension of 5-dimethylamino-2-nitro-benzoic acid methyl ester (400 mg, 1.78 mmol) in methanol (20 mL) and hydrogenated under atmospheric pressure at room temperature for 2 hr. The reaction mixture was filtered over celite and the filtrate was concentrated in vacuum to afford methyl 2-amino-5-dimethylamino-benzoic acid methyl ester (340 mg, 98%) as greenish brown liquid.

Reference Example 5

2-Mercapto-3-(2-methoxy-phenyl)-7-methyl-3H-quinazolin-4-one

1-Isothiocyanato-2-methoxy-benzene (0.76 mL, 5.45 mmol) was added to a solution of 2-amino-4-methyl-benzoic acid methyl ester (900 mg, 5.45 mmol) and acetic acid (1.5 mL) in ethanol (10 mL), and heated at reflux for 16 hr. The reaction mixture was cooled to room temperature and diluted with ethanol. The precipitated solid was filtered, washed with ethanol and dried to afford 2-mercapto-3-(2-methoxy-phenyl)-7-methyl-3H-quinazolin-4-one (1.0 g, 62%) as white solid.

Reference Example 5a to 5f

The compounds set out below were prepared in a manner analogous to Reference Example 5:

| Reference Example | Compound |
| --- | --- |
| 5a | 2-Mercapto-3-(2-methoxy-phenyl)-6-methyl-3H-quinazolin-4-one |
| 5b | 2-Mercapto-3-(2-methoxy-phenyl)-5-methyl-3H-quinazolin-4-one |
| 5c | 2-Mercapto-5-methoxy-3-(2-methoxy-phenyl)-3H-quinazolin-4-one |
| 5d | 6-Dimethylamino-2-mercapto-3-(2-methoxy-phenyl)-3H-quinazolin-4-one |
| 5e | 2-Mercapto-3-(2-methoxy-phenyl)-3H-quinazolin-4-one |
| 5f | 2-Mercapto-6-methoxy-3-(2-methoxy-phenyl)-3H-quinazolin-4-one |

Reference Example 6

3-(2-Isopropyl-phenyl)-2-mercapto-3H-quinazolin-4-one

2-Isothiocyanato-benzoic acid methyl ester (0.58 mL, 3.69 mmol) was added to a solution of 2-isopropyl aniline (500 mg, 3.69 mmol) and sodium methoxide (10 mg) in 2-propanol (10 mL) at room temperature and heated at reflux for 16 hr. The reaction mixture was concentrated to dryness under vacuum. The crude material was washed with dichloromethane (2×10 mL), 10% methanol in chloroform (2×10 mL) and dried under reduced pressure to afford 3-(2-isopropyl-phenyl)-2-mercapto-3H-quinazolin-4-one (600 mg, 55%) as white solid.

Reference Example 6a to 6b

The compounds set out below were prepared in a manner analogous to Reference Example 6:

| Reference Example | Compound |
|---|---|
| 6a | 3-(2-Ethyl-phenyl)-2-mercapto-3H-quinazolin-4-one |
| 6b | 3-(2-Dimethylamino-phenyl)-2-mercapto-3H-quinazolin-4-one |

Compound Example 1

2-Isopropylsulfanyl-3-(2-methoxy-phenyl)-7-methyl-3H-quinazolin-4-one

Isopropyl bromide (0.11 mL, 1.25 mmol) was added to a suspension of 2-mercapto-3-(2-methoxy-phenyl)-7-methyl-3H-quinazolin-4-one (250 mg, 0.84 mmol) and potassium carbonate (235 mg, 1.68 mmol) in acetone (10 mL) and the mixture was heated at reflux for 16 hr. The reaction mixture was cooled to room temperature and the any solid were filtered and washed with acetone. The filtrate was concentrated to dryness in vacuo and the crude compound was purified by column chromatography over silica gel (100-200 mesh) using 5% ethyl acetate in pet ether as eluent to afford 2-isopropyl-sulfanyl-3-(2-methoxy-phenyl)-7-methyl-3H-quinazolin-4-one (170 mg, 59%) as semi solid.

Compound Examples 2 to 15

Compound Examples 2 to 15 listed above were prepared in a manner analogous to Compound Example 1.

TABLE 4

| Compound Example | NMR Data | MS Spectrum |
|---|---|---|
| 1 | $^1$H NMR (400 MHz, CDCl$_3$) δ 8.12 (d, 1H), 7.48 (t, 1H), 7.40 (s, 1H), 7.22 (t, 2H), 7.09-7.04 (m, 2H), 4.02 (sep, 1H), 3.78 (s, 3H), 2.49 (s, 3H), 1.36 (m, 6H) | 341 (M + H) |
| 2 | $^1$H NMR (400 MHz, CDCl$_3$) δ 8.02 (s, 1H), 7.52-7.47 (m, 3H), 7.21 (dd, 1H), 7.10-7.05 (m, 2H), 4.03 (sep, 1H), 3.79 (s, 3H), 2.45 (s, 3H), 1.39 (d, 3H), 1.37 (d, 3H) | 341 (M + H) |
| 3 | $^1$H NMR (400 MHz, CDCl$_3$) δ 7.56-7.43 (m, 3H), 7.22-7.20 (dd, 1H), 7.14-7.05 (m, 3H), 4.02 (sep, 1H), 3.81 (s, 3H), 2.81 (s, 3H), 1.37-1.34 (m, 6H) | 341 (M + H) |
| 4 | $^1$H NMR (400 MHz, CDCl$_3$) δ 7.60 (t, 1H), 7.46 (t, 1H), 7.17 (m, 2H), 7.07-7.01 (m, 2H), 6.78 (d, 1H), 4.00 (sep, 1H), 3.93 (s, 3H), 3.77 (s, 3H), 1.35 (m, 6H) | 357 (M + H) |
| 5 | $^1$H NMR (400 MHz, CDCl$_3$) δ 8.12 (d, 1H), 7.49 (t, 1H), 7.41 (s, 1H), 7.24-7.18 (m, 2H), 7.09-7.04 (m, 2H), 3.79 (s, 3H), 3.14 (m, 2H), 2.49 (s, 3H), 1.36 (t, 3H). | 327 (M + H). |
| 6 | $^1$H NMR (400 MHz, CDCl$_3$) δ 7.52-7.46 (m, 2H), 7.41 (s, 1H), 7.21 (d, 2H), 7.09-7.04 (m, 2H), 4.00 (sep, 1H), 3.78 (s, 3H), 3.03 (s, 6H), 1.38 (d, 3H), 1.35 (d, 3H) | 370 (M + H). |
| 7 | $^1$H NMR (400 MHz, CDCl$_3$) δ 8.24 (dd, 1H), 7.71 (m, 1H), 7.59 (d, 1H), 7.50 (m, 1H), 7.37 (m, 1H), 7.21 (dd, 1H), 7.11-7.06 (m, 2H), 4.04 (sep, 1H), 3.79 (s, 3H), 1.38 (d, 3H), 1.36 (d, 3H) | 327 (M + H) |
| 8 | $^1$H NMR (400 MHz, CDCl$_3$) δ 8.25 (d, 1H), 7.73 (t, 1H), 7.61 (d, 1H), 7.54-7.47 (m, 2H), 7.41-7.31 (m, 2H), 7.14 (d, 1H), 4.05 (sep, 1H), 2.68 (sep, 1H), 1.40-1.35 (m, 6H), 1.25 (d, 3H), 1.15 (d, 3H) | 339 (M + H) |
| 9 | $^1$H NMR (400 MHz, CDCl$_3$) δ 8.23 (d, 1H), 7.73 (t, 1H), 7.61 (d, 1H), 7.51-7.33 (m, 4H), 7.16 (d, 1H), 4.05 (sep, 1H), 2.45 (q, 2H), 1.36 (d, 6H), 1.19 (t, 3H) | 325 (M + H) |
| 10 | $^1$H NMR (400 MHz, CDCl$_3$) δ 7.61 (d, 1H), 7.55-7.48 (m, 2H), 7.33-7.30 (dd, 1H), 7.23-7.21 (dd, 1H), 7.11-7.06 (m, 2H), 4.01 (sep, 1H), 3.89 (s, 3H), 3.79 (s, 3H), 1.36 (m, 6H). | 357 (M + H) |
| 11 | $^1$H NMR (400 MHz, CDCl$_3$) δ 8.26 (d, 1H), 7.71 (t, 1H), 7.60 (d, 1H), 7.45-7.35 (m, 2H), 7.17-7.06 (m, 3H), 4.06 (sep, 1H), 2.65 (s, 6H), 1.38 (d, 3H), 1.35 (d, 3H) | 340 (M + H) |
| 12 | $^1$H NMR (400 MHz, CDCl$_3$) δ 7.60 (t, 1H), 7.47 (t, 1H), 7.20-7.17 (m, 2H), 7.08-7.02 (m, 2H), 6.79 (d, 1H), 3.94 (s, 3H), 3.78 (s, 3H), 3.15-3.11 (m, 2H), 1.33 (t, 3H) | 343 (M + H) |
| 13 | $^1$H NMR (400 MHz, CDCl$_3$) δ 8.25 (d, 1H), 7.73 (t, 1H), 7.62 (d, 1H), 7.51-7.33 (m, 4H), 7.18 (d, 1H), 3.16 (m, 2H), 2.46 (q, 2H), 1.34 (t, 3H), 1.21 (t, 3H) | 311 (M + H) |
| 14 | $^1$H NMR (400 MHz, CDCl$_3$) δ 7.56-7.43 (m, 3H), 7.22 (d, 1H), 7.14-7.05 (m, 3H), 3.80 (s, 3H), 3.14 (m, 2H), 2.81 (s, 3H), 1.33 (t, 3H) | 327 (M + H) |
| 15 | $^1$H NMR (400 MHz, CDCl$_3$) δ 8.26 (d, 1H), 7.76-7.71 (m, 1H), 7.62 (d, 1H), 7.52-7.47 (m, 2H), 7.41-7.31 (m, 2H), 7.15 (d, 1H), 3.23-3.09 (m, 2H), 2.65 (sep, 1H), 1.33 (t, 3H), 1.25 (d, 3), 1.15 (d, 3H) | 325 (M + H) |

Example 4

Measurement of Minimum Inhibitory Concentrations (MICs)

The compounds of Example 3 were assessed for anti-fungal activity as follows:

Between 1 and 5 mgs of compound were accurately weighed out into a sterile Eppendorf tube. The compound was dissolved in DMSO to give a solution containing 5 mg/mL. Tubes were stored at −20° C. until required.

On the day of testing thawed solutions were vortex mixed to ensure homogeneity. 30 µL of solution was removed and added to 570 µL of sterile water in a separate sterile Eppendorf. The thoroughly mixed solution was used to prepare a series of doubling dilutions in water, in a deep well plate. Thirteen replicate plates were prepared using a Minitrak by aspirating 20 µL from each well into eleven clear polystyrene 96 well plates.

Spores of *Aspergillus* spp. (*Aspergillus fumigatus* [two strains], *Aspergillus terreus* [two strains], *Aspergillus niger* and *Aspergillus flavus*) were harvested from cultures grown on Sabarauds agar for 5 days, and resuspended in PBS/Tween 80 to approx $1 \times 10^7$ cfu/mL. Each organism suspension was diluted in YAG medium (1% glucose, 1% ammonium chloride and 0.5% yeast extract) to $0.5-2 \times 10^4$ cfu/mL. 80 µL of an organism suspension was added to each well of the plate containing drug dilutions.

This produced MIC plates with a drug range 50-0.05 mg/L and organism inocula of $1-2 \times 10^4$ cfu/mL for *Aspergillus* spp. All plates were incubated for 24 hrs at 35° C. Growth was assessed by monitoring the optical density at 485 nm for each well. The MIC of a compound is the lowest drug concentration that inhibits growth of an organism by >70% compared with a drug free control. MICs are recorded as mg/L. In cases where the MIC of an organism is >=0.05 mg/L the MIC is repeated using a concentration range of 0.5-0.0005 mg/L.

Assays were also performed in RPMI medium. To perform MIC tests in this medium, dilutions of compounds are prepared in microtitre plates as described above. Fungal strains to be tested are grown and harvested in an identical manner to that described above, and each organism suspension was diluted in RPMI medium, containing 2% glucose and 0.135 M MOPS buffer (pH 7.0) to $0.5-2 \times 10^4$ cfu/mL, rather than in YAG medium. 80 µL of an organism suspension was added to each well of the plate containing drug dilutions.

This produced MIC plates with a drug range 50-0.05 mg/L and organism inocula of $1-2 \times 10^4$ cfu/mL. All plates were incubated for 24-48 hrs at 35° C. Growth was assessed by monitoring the optical density at 485 nm for each well. The MIC of a compound is the lowest drug concentration that inhibits growth of an organism by >80% compared with a drug free control. The following organisms were tested: *Aspergillus flavus*, *Aspergillus fumigatus* AF293 and AF210, *Aspergillus niger* and *Aspergillus terreus* AT4 and AT49.

Other fungi including *Absidia corymbifera*; *Acremonium* spp; *Alternaria alternata*; *Aspergillus nidulans*; *Aspergillus parasiticus*; *Bipolaris* spp; *Blastomyces dermatitidis*; *Blumeria graminis*; *Candida albicans*; *Candida glabrata*; *Candida krusei*; *Candida parapsilosis*; *Candida tropicalis*; *Cladosporium cladosporoides*; *Cladosporium herbarium*; *Coccidioides immitis*; *Coccidioides posadasii*; *Colletotrichium trifolii*; *Curvularia lunata*; *Colletotrichium trifolii*; *Cryptococcus neoformans*; *Encephalitozoon cuniculi*; *Epicoccum nigrum*; *Epidermophyton floccosum*; *Exophiala* spp; *Exserohilum rostratum*; *Fusarium graminearium*; *Fusarium solani*; *Fusarium sporotrichoides*; *Histoplasma capsulatum*; *Leptosphaeria nodorum*; *Magnaporthe grisea*; *Microsporum canis*; *Mycosphaerella graminicola*; *Neurospora crassa*; *Paecilomyces lilanicus*; *Paecilomyces varioti*; *Penicillium chrysogenum*; *Phytophthora capsici*; *Phytophthora infestans*; *Plasmopara viticola*; *Pneumocystis jiroveci*; *Puccinia coronata*; *Puccinia graminis*; *Pyricularia oryzae*; *Pythium ultimum*; *Rhizomucor* sp.; *Rhizoctonia solani*; *Rhizomucor* spp.; *Rhizopus* spp.; *Scedosporium apiospermum*; *Scedosporium prolificans*; *Scopulariopsis brevicaulis*; *Trichophyton interdigitale*; *Trichophyton mentagrophytes*; *Trichophyton rubrum*; *Trichosporon asahii*; *Trichosporon beigelii*; and *Ustilago maydis* may also be used in the above assay. Fungi are cultured by standard methods known to those skilled in the art, and MICs determined as above.

MIC Results in mg/L (YAG Medium):

The following MIC results have been banded into grades. Thus, a grade of 1 represents an MIC of greater than 10 mg/L. A grade of 2 represents an MIC of from 1 to 10 mg/L. A grade of 3 represents an MIC of less than 1 mg/L.

TABLE 5

| Example no. | A. flavus | A. fumigatus | A. fumigatus 210 | A. niger | A. terreus | A. terreus 49 |
|---|---|---|---|---|---|---|
| 1 | 3 | 3 | 3 | 3 | 3 | 3 |
| 2 | 1 | 3 | 3 | 3 | 3 | 3 |
| 3 | 1 | 3 | 3 | 3 | 3 | 3 |
| 4 | 2 | 3 | 3 | 3 | 3 | 3 |
| 5 | 3 | 3 | 3 | 3 | 3 | 3 |
| 6 | 1 | 2 | 2 | 3 | 2 | 2 |
| 7 | 1 | 3 | 3 | 3 | 3 | 2 |
| 8 | 1 | 3 | 3 | 3 | 3 | 3 |
| 9 | 1 | 3 | 3 | 3 | 2 | 3 |
| 10 | 1 | 2 | 2 | 3 | 2 | 3 |
| 11 | 1 | 2 | 2 | 2 | 2 | 2 |
| 12 | 2 | 3 | 3 | 3 | 2 | 3 |
| 13 | 1 | 2 | 2 | 3 | 2 | 2 |
| 14 | 2 | 3 | 3 | 3 | 3 | 3 |
| 15 | 1 | 3 | 3 | 3 | 2 | 3 |

MIC Results in mg/L (RPMI Medium):
The following MIC results have been banded into grades as defined above.

TABLE 6

| Example no. | A. flavus | A. fumigatus | A. fumigatus 210 | A. niger | A. terreus | A. terreus 49 |
|---|---|---|---|---|---|---|
| 1 | 1 | 2 | 2 | 1 | 3 | 3 |
| 2 | 1 | 2 | 2 | 3 | 1 | 2 |
| 3 | 1 | 2 | 2 | 3 | 1 | 2 |
| 4 | 1 | 3 | 2 | 3 | 2 | 2 |
| 5 | 1 | 2 | 2 | 1 | 2 | 2 |
| 6 | 1 | 1 | 2 | 3 | 1 | 1 |
| 7 | 1 | 2 | 2 | 3 | 2 | 2 |
| 8 | 1 | 3 | 2 | 3 | 1 | 2 |
| 9 | 1 | 3 | 1 | 3 | 1 | 1 |
| 10 | 1 | 1 | 1 | 2 | 1 | 1 |
| 11 | 1 | 2 | 1 | 2 | 1 | 1 |
| 12 | 1 | 2 | 2 | 3 | 2 | 2 |
| 13 | 1 | 2 | 1 | 2 | 1 | 1 |
| 14 | 1 | 2 | 2 | 3 | 1 | 2 |
| 15 | 1 | 3 | 2 | 3 | 1 | 1 |

Example 5

Physical Properties of Preferred Inhibitors with High Activity

High activity inhibitors had the following properties:
IC 50 (concentration of inhibitor that inhibits enzyme activity by 50%) of 10 nM to 100 nM (and often 20 nM to 100 nM),
Ki of 20 nM to 60 nm,
binding to DHODH which is reversible and competitive with coenzyme Q cosubstrate (indicating binding of the inhibitor within the quinone pocket of DHODH).
For the DHODH enzyme of *A. fumigatus*, the following regions contribute to the quinone pocket environment:
Valine 87 to glutamic acid 135
Valine 144 to leucine 218
Asparagine 487 to arginine 530.
For the DHODH enzyme of *C. albicans*, the following regions contribute to the quinone pocket environment:
Tyrosine 52 to leucine 95
Valine 106 to serine 180
Asparagine 388 to glutamic acid 431.

SEQUENCE LISTING

SEQ ID No1.
*Aspergillus fumigatus* DHODH
MVANSTSLAWKSAGLRARAVPSLRCSHRSSVLHRQAAFQQHGAVRHASS

TTSEAAEAVKEAPKKAGRGLKRTVYGTSLVLAALVGYVYATDTRASIHR

YAVVPLVRTLYPDAEEAHHIGVEALKTLYKYGLHPRERGNQDGDGVLAT

EVFGYTLNNPIGISGGLDKHAEIPDPLFAIGPAIVEVGGTTPLPQEGNP

RPRVFRLPSQKAMINRYGLNSLGADHMAAILERRVRDFAYANGFGLHDE

AEQRVLDGEAGVPPGSLQPGRLLAVQIAKNKATPDSDIEAIKRDYVYCV

DRLAKYADILVVNVSSPNTGLRDLQATAPLTAILKAVVSAAKGVDRKTK

PYVMVKVSPDEDSDEQSGICDAVWHSGVDGVIVGNTTNRRPAPLPHGFT

LPPKEQSTLKETGGYSGPQLFDRTAALVARYRALLDAPPTPASDANETD

QAKELAAAVTRAEPDVENVPAVEPPTPANRPARKVIFASGGITNGKQAQ

AVLDAGASVAMMYTAVTYGGIGTVTRVKQELREEKKNRQ

SEQUENCE LISTING

SEQ ID No. 2
*Candida albicans* DHODH
MFRPSIKFKQSTLSIIARRLKSSAQHQPLRSSFVPSPIVFVAGLAVAAV

GGYYCLDSRSAIHEYVLCPLIRTFTDAESGHKLGIFFMKYGLSPRLLDD

GKNDQSDVLGVQVFGHKLKNPIGLAAGLDKDGEAIESLFNCGFSYVEIG

SITPEPQPGNPQPRFFRLPKDDAVINRYGFNSSGHFNVLATLKLRFNKL

LNKFGTSHSSEQHPFSNAFQQGKLLGINLGKNKFGDEVNDYVKGVERLG

PYADVLVINVSSPNTGLRDLQSEAKLTNLLTTVVKERNVLGKNLLGNK

PPVLVKVAPDLTEPEIESIANSAKEAKVDGIIISNTTIQRPVDRLLTTD

KQLINQAGGLSGKPLKPLSLKALRTLRKYTKDSDLVLIGCGGISNGKDA

LEFGKAGATFIELYTAFAYKGPGLVGKIRDELAEELRKEGKTWEQIIGS

DDK

SEQ ID No. 3
GACGACGACAAGATGGCGACGGATACCAGGGCAAG

SEQ ID No. 4
GAGGAGAAGCCCGGTCTATTGACGGTTTTTCTTTTCC

SEQ ID No. 5:
GACGACGACAAGATGGCCACGGGAGATGAGCG

SEQ ID No. 6:
GAGGAGAAGCCCGGTTCACCTCCGATGATCTGCTC

SEQ ID No. 7:
GACGACGACAAGATGACGGCCACAGGGGATGAC

SEQ ID No. 8:
GAGGAGAAGCCCGGTTCACCTCCGATGATCTGCTC

SEQ ID No. 9:
GACGACGACAAGATGTCAAGATCAGCAATCCATGA

SEQ ID No. 10:
GAGGAGAAGCCCGGTTCACTTATCATCAGAGCCAA

SEQ ID No. 11:
MAWRHLKKRAQDAVIILGGGGLLFASYLMATGDERFYAEHLMPTLQGLL

DPESAHRLAVRFTSLGLLPRARFQDSDMLEVRVLGHKFRNPVGIAAGFD

KHGEAVDGLYKMGFGFVEIGSVTPKPQEGNPRPRVFRLPEDQAVINRYG

FNSHGLSVVEHRLRARQQKQAKLTEDGLPLGVNLGKNKTSVDAAEDYAE

GVRVLGPLADYLVVNVSSPNTAGLRSLQGKAELRRLLTKVLQERDGLRR

VHRPAVLVKIAPDLTSQDKEDIASVVKELGIDGLIVTNTTVSRPAGLQG

ALRSETGGLSGKPLRDLSTQTIREMYALTQGRVPIIGVGGVSSGQDALE

KIRAGASLVQLYTALTFWGPPVVGKVKRELEALLKEQGFGGVTDAIGAD

HRR

The invention claimed is:

1. A method of identifying an antifungal agent which targets a dihydroorotate dehydrogenase (DHODH) protein of a fungus comprising contacting a candidate substance with a fungal DHODH protein and determining whether the candidate substance inhibits the DHODH protein, wherein inhibition indicates that the candidate substance is an antifungal agent and wherein inhibition of the DHODH protein is measured by the addition of (a) ubiquinone 5 (coenzyme Q1) or ubiquinone 10 (coenzyme Q2) and (b) an electron acceptor and detecting the reduction of the electron acceptor.

2. A method according to claim 1 comprising wherein the DHODH protein is
   (i) a DHODH protein which comprises the amino acid sequence shown by SEQ ID NO:1 or 2; or
   (ii) a protein which has at least 50% identity with (i); or
   (iii) a protein comprising a variant and/or fragment of (i) or (ii) which fragment has a length of at least 50 amino acids.

3. A method according to claim 1 wherein the candidate compound is contacted with said DHODH protein under assay conditions of, optionally, 500 µM dihydroorotate, and/or 50 µM quinone, and/or 100 µM 2,6-dichloroindophenol, and/or at a DHODH enzyme concentration such that the enzyme activity is in a linear range with respect to time and protein concentration, and/or at pH 8.0, and/or in 150 mM NaCl, and/or in 50 mM Tris.HCl, and/or with 1% DMSO, and/or with 8% volume to volume (v/v) glycerol, and/or with 0.08% v/v Triton X-100, and/or incubated at room temperature, and/or incubated for 20-40 minutes, and/or where the assay has a dynamic range (Z') value of ≥0.375, and/or where the assay has a coefficient of variation (% CV) value of <5% for minus-enzyme or completely-inhibited control.

4. A method according to claim 1 wherein the fungal DHODH protein comprises the amino acid sequence shown by SEQ ID NO:1 or SEQ ID NO: 2.

5. A method according to claim 1, wherein the fungal DHODH protein has an amino acid sequence which shares at least 50% identity with the amino acid sequence shown by SEQ ID NO:1 or SEQ ID NO: 2.

6. A method according to claim 1 wherein the DHODH protein comprises a fragment and/or a variant and/or a fusion protein of DHODH.

7. A method according to claim 1, wherein the fungal DHODH protein is from *Aspergillus* or *Candida* species, and/or wherein the method is capable of determining the IC50 and/or Ki of the candidate substance, wherein optionally the candidate compound is selected based on having an IC 50 of 10 nM to 100 nM and/or a Ki of 20 nM to 60 nm and/or binding to DHODH protein which is reversible and/or binding to DHODH protein which is competitive with coenzyme Q cosubstrate.

8. A method according to claim 1 wherein the candidate substance is also contacted with a mammalian DHODH which comprises
   (i) the amino acid sequence shown by SEQ ID NO: 11; or
   (ii) a protein which has at least 80% identity with mammalian DHODH, or
   (iii) a protein comprising a fragment or variant of the mammalian DHODH;

which fragment has a length of at least 50 amino acids, and the activity of the mammalian DHODH in the presence of the compound is determined.

* * * * *

SEQUENCE LISTING

<160> NUMBER OF SEQ ID NOS: 11

<210> SEQ ID NO 1
<211> LENGTH: 531
<212> TYPE: PRT
<213> ORGANISM: Aspergillus fumigatus

<400> SEQUENCE: 1

```
Met Val Ala Asn Ser Thr Ser Leu Ala Trp Lys Ser Ala Gly Leu Arg
1               5                   10                  15

Ala Arg Ala Val Pro Ser Leu Arg Cys Ser His Arg Ser Ser Val Leu
            20                  25                  30

His Arg Gln Ala Ala Phe Gln Gln His Gly Ala Val Arg His Ala Ser
        35                  40                  45

Ser Thr Thr Ser Glu Ala Ala Glu Ala Val Lys Glu Ala Pro Lys Lys
    50                  55                  60

Ala Gly Arg Gly Leu Lys Arg Thr Val Tyr Gly Thr Ser Leu Val Leu
65                  70                  75                  80

Ala Ala Leu Val Gly Tyr Val Tyr Ala Thr Asp Thr Arg Ala Ser Ile
                85                  90                  95

His Arg Tyr Ala Val Val Pro Leu Val Arg Thr Leu Tyr Pro Asp Ala
            100                 105                 110

Glu Glu Ala His His Ile Gly Val Glu Ala Leu Lys Thr Leu Tyr Lys
        115                 120                 125

Tyr Gly Leu His Pro Arg Glu Arg Gly Asn Gln Asp Gly Asp Gly Val
    130                 135                 140

Leu Ala Thr Glu Val Phe Gly Tyr Thr Leu Asn Asn Pro Ile Gly Ile
145                 150                 155                 160

Ser Gly Gly Leu Asp Lys His Ala Glu Ile Pro Asp Pro Leu Phe Ala
                165                 170                 175

Ile Gly Pro Ala Ile Val Glu Val Gly Gly Thr Thr Pro Leu Pro Gln
            180                 185                 190

Glu Gly Asn Pro Arg Pro Arg Val Phe Arg Leu Pro Ser Gln Lys Ala
        195                 200                 205

Met Ile Asn Arg Tyr Gly Leu Asn Ser Leu Gly Ala Asp His Met Ala
    210                 215                 220

Ala Ile Leu Glu Arg Arg Val Arg Asp Phe Ala Tyr Ala Asn Gly Phe
225                 230                 235                 240

Gly Leu His Asp Glu Ala Glu Gln Arg Val Leu Asp Gly Glu Ala Gly
                245                 250                 255

Val Pro Pro Gly Ser Leu Gln Pro Gly Arg Leu Leu Ala Val Gln Ile
            260                 265                 270

Ala Lys Asn Lys Ala Thr Pro Asp Ser Asp Ile Glu Ala Ile Lys Arg
        275                 280                 285
```

-continued

```
Asp Tyr Val Tyr Cys Val Asp Arg Leu Ala Lys Tyr Ala Asp Ile Leu
    290                 295                 300

Val Val Asn Val Ser Ser Pro Asn Thr Pro Gly Leu Arg Asp Leu Gln
305                 310                 315                 320

Ala Thr Ala Pro Leu Thr Ala Ile Leu Lys Ala Val Val Ser Ala Ala
                325                 330                 335

Lys Gly Val Asp Arg Lys Thr Lys Pro Tyr Val Met Val Lys Val Ser
                340                 345                 350

Pro Asp Glu Asp Ser Asp Glu Gln Val Ser Gly Ile Cys Asp Ala Val
            355                 360                 365

Trp His Ser Gly Val Asp Gly Val Ile Val Gly Asn Thr Thr Asn Arg
    370                 375                 380

Arg Pro Ala Pro Leu Pro His Gly Phe Thr Leu Pro Pro Lys Glu Gln
385                 390                 395                 400

Ser Thr Leu Lys Glu Thr Gly Gly Tyr Ser Gly Pro Gln Leu Phe Asp
                405                 410                 415

Arg Thr Ala Ala Leu Val Ala Arg Tyr Arg Ala Leu Leu Asp Ala Pro
                420                 425                 430

Pro Thr Pro Ala Ser Asp Ala Asn Glu Thr Asp Gln Ala Lys Glu Leu
            435                 440                 445

Ala Ala Ala Val Thr Arg Ala Glu Pro Asp Val Glu Asn Val Pro Ala
450                 455                 460

Val Glu Pro Pro Thr Pro Ala Asn Arg Pro Ala Arg Lys Val Ile Phe
465                 470                 475                 480

Ala Ser Gly Gly Ile Thr Asn Gly Lys Gln Ala Gln Ala Val Leu Asp
                485                 490                 495

Ala Gly Ala Ser Val Ala Met Met Tyr Thr Ala Val Thr Tyr Gly Gly
            500                 505                 510

Ile Gly Thr Val Thr Arg Val Lys Gln Glu Leu Arg Glu Glu Lys Lys
    515                 520                 525

Asn Arg Gln
    530

<210> SEQ ID NO 2
<211> LENGTH: 444
<212> TYPE: PRT
<213> ORGANISM: Candida albicans

<400> SEQUENCE: 2

Met Phe Arg Pro Ser Ile Lys Phe Lys Gln Ser Thr Leu Ser Ile Ile
1               5                   10                  15

Ala Arg Arg Leu Lys Ser Ser Ala Gln His Gln Pro Leu Arg Ser Ser
                20                  25                  30

Phe Val Pro Ser Pro Ile Val Phe Val Ala Gly Leu Ala Val Ala Ala
            35                  40                  45

Val Gly Gly Tyr Tyr Cys Leu Asp Ser Arg Ser Ala Ile His Glu Tyr
        50                  55                  60

Val Leu Cys Pro Leu Ile Arg Thr Phe Thr Asp Ala Glu Ser Gly His
65                  70                  75                  80

Lys Leu Gly Ile Phe Phe Met Lys Tyr Gly Leu Ser Pro Arg Leu Leu
                85                  90                  95

Asp Asp Gly Lys Asn Asp Gln Ser Asp Val Leu Gly Val Gln Val Phe
            100                 105                 110

Gly His Lys Leu Lys Asn Pro Ile Gly Leu Ala Ala Gly Leu Asp Lys
        115                 120                 125
```

Asp Gly Glu Ala Ile Glu Ser Leu Phe Asn Cys Gly Phe Ser Tyr Val
130                 135                 140

Glu Ile Gly Ser Ile Thr Pro Glu Pro Gln Pro Gly Asn Pro Gln Pro
145                 150                 155                 160

Arg Phe Phe Arg Leu Pro Lys Asp Asp Ala Val Ile Asn Arg Tyr Gly
                165                 170                 175

Phe Asn Ser Ser Gly His Phe Asn Val Leu Ala Thr Leu Lys Leu Arg
            180                 185                 190

Phe Asn Lys Leu Leu Asn Lys Phe Gly Thr Ser His Ser Ser Glu Gln
        195                 200                 205

His Pro Phe Ser Asn Ala Phe Gln Gln Gly Lys Leu Leu Gly Ile Asn
210                 215                 220

Leu Gly Lys Asn Lys Phe Gly Asp Glu Val Asn Asp Tyr Val Lys Gly
225                 230                 235                 240

Val Glu Arg Leu Gly Pro Tyr Ala Asp Val Leu Val Ile Asn Val Ser
                245                 250                 255

Ser Pro Asn Thr Pro Gly Leu Arg Asp Leu Gln Ser Glu Ala Lys Leu
            260                 265                 270

Thr Asn Leu Leu Thr Thr Val Val Lys Glu Arg Asn Val Leu Gly Lys
        275                 280                 285

Asn Leu Leu Gly Asn Lys Pro Pro Val Leu Val Lys Val Ala Pro Asp
290                 295                 300

Leu Thr Glu Pro Glu Ile Glu Ser Ile Ala Asn Ser Ala Lys Glu Ala
305                 310                 315                 320

Lys Val Asp Gly Ile Ile Ile Ser Asn Thr Thr Ile Gln Arg Pro Val
                325                 330                 335

Asp Arg Leu Leu Thr Thr Asp Lys Gln Leu Ile Asn Gly Ala Gly Gly
            340                 345                 350

Leu Ser Gly Lys Pro Leu Lys Pro Leu Ser Leu Lys Ala Leu Arg Thr
        355                 360                 365

Leu Arg Lys Tyr Thr Lys Asp Ser Asp Leu Val Leu Ile Gly Cys Gly
370                 375                 380

Gly Ile Ser Asn Gly Lys Asp Ala Leu Glu Phe Gly Lys Ala Gly Ala
385                 390                 395                 400

Thr Phe Ile Glu Leu Tyr Thr Ala Phe Ala Tyr Lys Gly Pro Gly Leu
                405                 410                 415

Val Gly Lys Ile Arg Asp Glu Leu Ala Glu Glu Leu Arg Lys Glu Gly
            420                 425                 430

Lys Thr Trp Glu Gln Ile Ile Gly Ser Asp Asp Lys
        435                 440

<210> SEQ ID NO 3
<211> LENGTH: 35
<212> TYPE: DNA
<213> ORGANISM: Artificial Sequence
<220> FEATURE:
<223> OTHER INFORMATION: Primer: JO_AFpyrEtr_F4

<400> SEQUENCE: 3
gacgacgaca agatggcgac ggataccagg gcaag                              35

<210> SEQ ID NO 4
<211> LENGTH: 37
<212> TYPE: DNA
<213> ORGANISM: Artificial Sequence
<220> FEATURE:

-continued

<223> OTHER INFORMATION: Primer: JO_AFpyrE_R3

<400> SEQUENCE: 4
gaggagaagc ccggtctatt gacggttttt cttttcc                37

<210> SEQ ID NO 5
<211> LENGTH: 32
<212> TYPE: DNA
<213> ORGANISM: Artificial Sequence
<220> FEATURE:
<223> OTHER INFORMATION: Primer: JO_hD licF2

<400> SEQUENCE: 5
gacgacgaca agatggccac gggagatgag cg                32

<210> SEQ ID NO 6
<211> LENGTH: 35
<212> TYPE: DNA
<213> ORGANISM: Artificial Sequence
<220> FEATURE:
<223> OTHER INFORMATION: Primer: JO_hD licR1

<400> SEQUENCE: 6
gaggagaagc ccggttcacc tccgatgatc tgctc                35

<210> SEQ ID NO 7
<211> LENGTH: 33
<212> TYPE: DNA
<213> ORGANISM: Artificial Sequence
<220> FEATURE:
<223> OTHER INFORMATION: Primer: JO_rD licF2

<400> SEQUENCE: 7
gacgacgaca agatgacggc cacaggggat gac                33

<210> SEQ ID NO 8
<211> LENGTH: 35
<212> TYPE: DNA
<213> ORGANISM: Artificial Sequence
<220> FEATURE:
<223> OTHER INFORMATION: Primer: JO rD licR1

<400> SEQUENCE: 8
gaggagaagc ccggttcacc tccgatgatc tgctc                35

<210> SEQ ID NO 9
<211> LENGTH: 35
<212> TYPE: DNA
<213> ORGANISM: Artificial Sequence
<220> FEATURE:
<223> OTHER INFORMATION: Primer: JO_CAD licF3

<400> SEQUENCE: 9
gacgacgaca agatgtcaag atcagcaatc catga                35

<210> SEQ ID NO 10
<211> LENGTH: 35
<212> TYPE: DNA
<213> ORGANISM: Artificial Sequence
<220> FEATURE:

<223> OTHER INFORMATION: Primer: JO_CAD licR1

<400> SEQUENCE: 10
gaggagaagc ccggttcact tatcatcaga gccaa                                35

<210> SEQ ID NO 11
<211> LENGTH: 395
<212> TYPE: PRT
<213> ORGANISM: Unknown
<220> FEATURE:
<223> OTHER INFORMATION: Mammalian DHODH

<400> SEQUENCE: 11

```
Met Ala Trp Arg His Leu Lys Lys Arg Ala Gln Asp Ala Val Ile Ile
 1               5                  10                  15

Leu Gly Gly Gly Gly Leu Leu Phe Ala Ser Tyr Leu Met Ala Thr Gly
                20                  25                  30

Asp Glu Arg Phe Tyr Ala Glu His Leu Met Pro Thr Leu Gln Gly Leu
            35                  40                  45

Leu Asp Pro Glu Ser Ala His Arg Leu Ala Val Arg Phe Thr Ser Leu
        50                  55                  60

Gly Leu Leu Pro Arg Ala Arg Phe Gln Asp Ser Asp Met Leu Glu Val
 65                  70                  75                  80

Arg Val Leu Gly His Lys Phe Arg Asn Pro Val Gly Ile Ala Ala Gly
                 85                  90                  95

Phe Asp Lys His Gly Glu Ala Val Asp Gly Leu Tyr Lys Met Gly Phe
            100                 105                 110

Gly Phe Val Glu Ile Gly Ser Val Thr Pro Lys Pro Gln Glu Gly Asn
        115                 120                 125

Pro Arg Pro Arg Val Phe Arg Leu Pro Glu Asp Gln Ala Val Ile Asn
130                 135                 140

Arg Tyr Gly Phe Asn Ser His Gly Leu Ser Val Val Glu His Arg Leu
145                 150                 155                 160

Arg Ala Arg Gln Gln Lys Gln Ala Lys Leu Thr Glu Asp Gly Leu Pro
                165                 170                 175

Leu Gly Val Asn Leu Gly Lys Asn Lys Thr Ser Val Asp Ala Ala Glu
            180                 185                 190

Asp Tyr Ala Glu Gly Val Arg Val Leu Gly Pro Leu Ala Asp Tyr Leu
        195                 200                 205

Val Val Asn Val Ser Ser Pro Asn Thr Ala Gly Leu Arg Ser Leu Gln
    210                 215                 220

Gly Lys Ala Glu Leu Arg Arg Leu Leu Thr Lys Val Leu Gln Glu Arg
225                 230                 235                 240

Asp Gly Leu Arg Arg Val His Arg Pro Ala Val Leu Val Lys Ile Ala
                245                 250                 255

Pro Asp Leu Thr Ser Gln Asp Lys Glu Asp Ile Ala Ser Val Val Lys
            260                 265                 270

Glu Leu Gly Ile Asp Gly Leu Ile Val Thr Asn Thr Thr Val Ser Arg
        275                 280                 285

Pro Ala Gly Leu Gln Gly Ala Leu Arg Ser Glu Thr Gly Gly Leu Ser
    290                 295                 300

Gly Lys Pro Leu Arg Asp Leu Ser Thr Gln Thr Ile Arg Glu Met Tyr
305                 310                 315                 320

Ala Leu Thr Gln Gly Arg Val Pro Ile Ile Gly Val Gly Gly Val Ser
                325                 330                 335
```

```
Ser Gly Gln Asp Ala Leu Glu Lys Ile Arg Ala Gly Ala Ser Leu Val
            340                 345             350

Gln Leu Tyr Thr Ala Leu Thr Phe Trp Gly Pro Pro Val Val Gly Lys
        355             360                 365

Val Lys Arg Glu Leu Glu Ala Leu Leu Lys Glu Gln Gly Phe Gly Gly
    370             375             380

Val Thr Asp Ala Ile Gly Ala Asp His Arg Arg
385                 390             395
```